US 7,141,562 B2
(12) United States Patent
Maag et al.

(10) Patent No.: US 7,141,562 B2
(45) Date of Patent: Nov. 28, 2006

(54) SUBSTITUTED BENZOXAZINONES AND USES THEREOF

(75) Inventors: Hans Maag, Sausalito, CA (US); Meng Sui, Union City, CA (US); Shu-Hai Zhao, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 22 days.

(21) Appl. No.: 10/702,302

(22) Filed: Nov. 6, 2003

(65) Prior Publication Data
US 2004/0092512 A1 May 13, 2004

Related U.S. Application Data

(60) Provisional application No. 60/424,946, filed on Nov. 8, 2002.

(51) Int. Cl.
C07D 413/04 (2006.01)
C07D 413/14 (2006.01)
A61K 31/538 (2006.01)

(52) U.S. Cl. .............................. 514/214.01; 514/230.5; 514/217.05; 514/221; 514/222.5; 540/491; 540/575; 540/593; 540/599; 540/567; 544/105; 544/2

(58) Field of Classification Search ................ 544/105; 514/230.5, 214.01, 217.05, 221; 540/567, 540/575, 593, 599
See application file for complete search history.

(56) References Cited

U.S. PATENT DOCUMENTS

| 5,424,313 | A | 6/1995 | Hartog et al. |
| 6,214,829 | B1 | 4/2001 | Feenstra et al. |
| 6,225,312 | B1 | 5/2001 | Feenstra et al. |

FOREIGN PATENT DOCUMENTS

| WO | WO 97/36893 A1 | 10/1997 |
| WO | WO 01/14330 A2 | 3/2001 |
| WO | WO 01/57003 A1 | 8/2001 |
| WO | WO 01/72725 A1 | 10/2001 |
| WO | WO 02/02529 A1 | 1/2002 |
| WO | WO 02/34754 A2 | 5/2002 |
| WO | WO 03/095434 A1 | 11/2003 |

OTHER PUBLICATIONS

Russell MG and Dias R. (Curr. Top. Med. Chem, Jun. 2002; 2(6):643-54).*
Thomas A. Godwin (Gastrointestinal Diseases, <http://edcenter.med.cornell.edu/CUMC_PathNotes/Gastrointestinal/Gastrointestinal.html>, 51 pages), downloaded on Jul. 7, 2005.*

Belliotti, T.R., et al, "A Series of 6- and 7-Piperazinyl- and-Piperidinylmethylbenzoxazinones with Dopamine D4 Antagonist Activity: Discovery of a Potential Atypical Antipsychotic Agent", *J. Med. Chem*, 1999, 42(25), pp. 5181-5187.

Gutschow, M., et al, Studies on 2-benzyloxy-4H-3,1-benzoxazine-4-ones as serine protease inhibitors:, *Pharmaceutica Acta Helvetiae*, 1999, 73(2), pp. 95-103.

Krantz, A., et al, "Design and Synthesis of 4H-3,1-Benzoxazine-4-ones as Potent Alternate Substrate Inhibitors of Human Leukocyte Elastase", *J. Med. Chem.*, 1990, 33(2), pp. 464-479.

Spencer, R.W., et al., "Inhibiton of Serine Proteases by Benzoxazinones: Effects of Electron Withdrawal and 5-Substitution", *Biochem Biophys Res. Commun*, 1986, 140(3), pp. 928-933.

Taverne, T., et al., "Novel Benzothiazolin-2-one and Benzoxazin-3-one-Arylpiperazine Derivatives with Mixed $5HT_{1A}/D_2$ Affinity as Potential Atypical Antipsychotics", *J. Med Chem*, 1998, 41(12), pp. 2010-2018.

Feenstra, Rolf W. et al., "New 1-Aryl-4-(biarylmethylene)piperazines as Potential Atypical Antipsychotics Sharing Dopamine $D_2$-Receptor and Serotonin $5\text{-}HT_{1A}$-Receptor Affinities," *Bioorganic & Medicinal Chemistry Letters*, (2001) pp. 2345-2349, No. 11, Pergamon.

* cited by examiner

*Primary Examiner*—Kahsay Habte
(74) *Attorney, Agent, or Firm*—Grant D. Green

(57) ABSTRACT

Compound of the Formula:

and pharmaceutically acceptable salts or prodrugs thereof, wherein: X is CH or N, Y is C or S, Z is $-SO_2-$ or $-(CR^aR^b)_r-$, n is 1 or 2, $R^2$ is aryl or heteroaryl, and $R^1$, $R^3$, $R^4$, $R^5$, $R^6$, $R^7$, $R^8$, $R^9$, $R^a$, $R^b$, m, p, q and r, are as defined herein. The compounds are modulators of the 5-HT6 receptor and are useful for treatment of central nervous system disorders. Also provided are methods for preparing, compositions comprising, and methods for using Compounds of Formula I.

30 Claims, No Drawings

SUBSTITUTED BENZOXAZINONES AND USES THEREOF

CROSS REFERENCE TO RELATED APPLICATIONS

This application is entitled to the benefit of U.S. Provisional Patent Application Ser. No. 60/424,946 filed on Nov. 8, 2002, the disclosure of which is incorporated herein by reference.

FIELD OF THE INVENTION

This invention relates to substituted benzoxazinone compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., *J. Pharmacol. Exp. Ther.*, 1994, 268, pages 1403–14120, D. R. Sibley et al., *Mol. Pharmacol.*, 1993, 43, 320–327, A. J. Sleight et al., *Neurotransmission*, 1995, 11, 1–5, and A. J. Sleight et al., *Serotonin ID Research Alert*, 1997, 2(3), 115–8.

While many 5-hydroxytryptamine modulators have been disclosed, there continues to be a need for compounds that are useful for modulating 5-HT2, 5-HT6 and other 5-HT receptors.

SUMMARY OF THE INVENTION

The invention provides a compound of the formula:

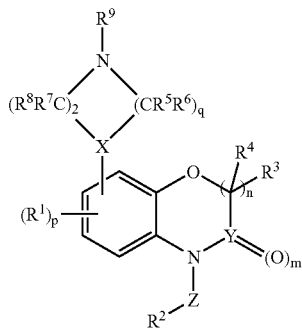

I and pharmaceutically acceptable salts or prodrugs thereof, wherein:

Y is C or S;
m is 1 when Y is C and m is 2 when Y is S;
n is 1 or 2;
p is from 0 to 3;
q is from 1 to 3;
Z is $-SO_2-$ or $-(CR^aR^b)_r-$ where each of $R^a$ and $R^b$ is independently hydrogen or alkyl;
r is from 0 to 2;
X is CH or N;
each $R^1$ is independently halo, alkyl, haloalkyl, hydroxy, heteroalkyl, alkoxy, cyano, $-S(O)_s-R^c$, $-C(=O)-NR^cR^d$, $-SO_2-NR^cR^d$, $-N(R^c)-C(=O)-R^d$, or $-C(=O)R^c$, where each of $R^c$ and $R^d$ is independently hydrogen or alkyl;
s is from 0 to 2.
$R^2$ is aryl or heteroaryl;
each of $R^3$ and $R^4$ is independently hydrogen, alkyl, hydroxyalkyl or alkoxyalkyl,
or $R^3$ and $R^4$ together with their shared carbon may form a ring of 3 to 6 members that optionally includes a nitrogen or oxygen heteroatom; and
each of $R^5$, $R^6$, $R^7$, $R^8$ and $R^9$ is independently hydrogen or alkyl, or one of $R^5$ and $R^6$ together with one of $R^7$, $R^8$ and $R^9$ together with the atoms therebetween may form a ring of 5 to 7 members.

The invention also provides methods for preparing, compositions comprising, and methods for using the aforementioned compounds. The methods of the invention comprise, in one embodiment, (a) contacting an N-arylalkyl benzoxazinone of the formula VI:

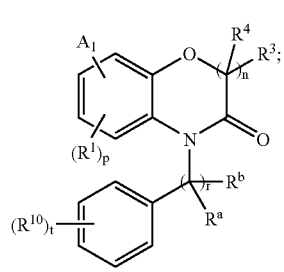

f wherein:
$A_1$ is a leaving group,
n is 1 or 2;
p is from 0 to 3;
r is from 0 to 2;
t is from 0 to 4;
each of $R^a$ and $R^b$ is independently hydrogen or alkyl;
each $R^1$ is independently halo, alkyl, haloalkyl, heteroalkyl, alkoxy, cyano, $-S(O)_s-R^c$, $-C(=O)-NR^cR^d$, $-SO_2-NR^cR^d$, $-N(R^c)-C(=O)-R^d$, or $-C(=O)R^c$,
where each of $R^c$ and $R^d$ is independently hydrogen or alkyl and s is from 0 to 2;
each of $R^3$ and $R^4$ is independently hydrogen or alkyl; and
each $R^{10}$ is independently halo, alkyl, alkoxy or cyano;

with a heterocyclic compound of the formula:

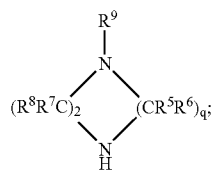

g wherein:
q is from 1 to 3; and
each of $R^5$, $R^6$, $R^7$, $R^8$ and $R^9$ is independently hydrogen or alkyl, or one of $R^5$ and $R^6$ together with one of $R^7$, $R^8$ and $R^9$ may form a ring of 5 to 7 members;

in the presence of a palladium catalyst to produce the heterocyclyl-substituted N-arylalkyl benzoxazinone compound of the formula:

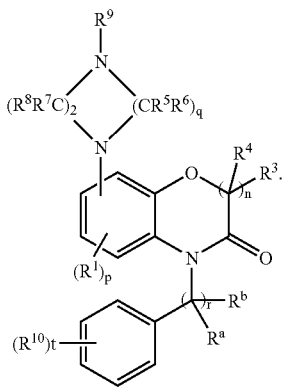

VI

The methods may further comprise:
(c) contacting a benzoxazinone of the formula:

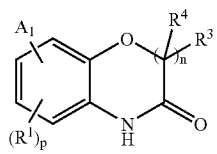

d wherein n, p, $A_1$, $R^1$, $R^3$ and $R^4$ are as defined above, with an alkylating agent of the formula:

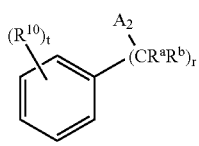

e wherein:
$A_2$ is a leaving group and may the same or different from $A_1$; and
r, t, $R^a$, $R^b$ and $R^{10}$ are as described in claim 41;

to produce the N-arylalkyl benzoxazinone of the formula VI:

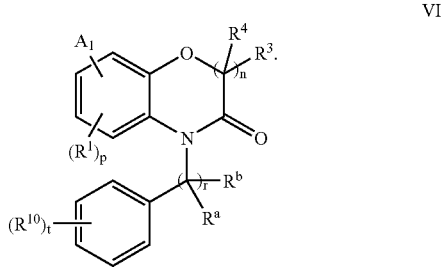

VI

DETAILED DESCRIPTION OF THE INVENTION

The invention provides substituted benzoxazinone compounds, associated compositions, methods for use as therapeutic agents, and methods of preparation thereof. In specific embodiments the invention provides piperazinyl-substituted benzo[1,4]oxazine-3-one compounds and associated pharmaceutical compositions, and methods for using the same in the treatment of CNS diseases and gastrointestinal tract disorders.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^aR^b$— wherein $R^a$ is alkoxy as defined herein and $R^b$ is alkylene as defined herein. Exemplary alkoxyalkyl moieties include methoxyethyl, ethoxyethyl, 2,3-dimethoxypropyl and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical —$R^aR^b$ where $R^a$ is an alkylene group and $R^b$ is an aryl group as defined herein; e.g., benzyl, phenylethyl, 3-(3-chlorophenyl)-2-methylpentyl, and the like are examples of arylalkyl.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Hydroxyalkyl" means a moiety of the formula HO—$R^c$— wherein $R^c$ is alkylene as defined herein. Exemplary hydroxyalkyl moieties include hydroxyethyl, hydroxypropyl, 2,3-dihydroxypropyl and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzoxazolyl, benzoxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Optionally substituted", when used in association with "aryl", "phenyl", "heteroaryl" or "heterocyclyl", means an aryl, phenyl, heteroaryl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, monoalkylamino, di-alkylamino, haloalkyl, haloalkoxy, heteroalkyl, —COR (where R is hydrogen, alkyl, phenyl or phenylalkyl), —$(CR'R")_n$—COOR (where n is an integer from 0 to 5, R' and R" are independently hydrogen or alkyl, and R is hydrogen, alkyl, cycloalkyl, cycloalkylalkyl, phenyl or phenylalkyl), or —$(CR'R")_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like;

or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p1–92, Elesevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. For convenience, the IUPAC numbering of the positions of representative benzoxazinone compounds described herein is shown by the formula:

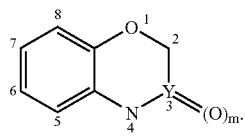

Compounds of the Invention

The invention provides compounds of the general formula:

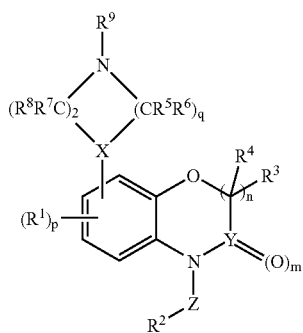

and pharmaceutically acceptable salts or prodrugs thereof, wherein:

Y is C or S; preferably Y is C;
m is 1 when Y=C, and m is 2 when Y=S;
n is 1 or 2; preferably n is 1;
p is from 0 to 3; preferably p is 1;
q is from 1 to 3; preferably q is 2;
Z is —$(CR^aR^b)_r$— or —$SO_2$— where each of $R^a$ and $R^b$ is independently hydrogen or alkyl; preferably Z is —$(CR^aR^b)_r$— and preferably $R^a$ and $R^b$ are hydrogen;

r is from 0 to 2; preferably r is 1;
X is CH or N; preferably X is N;
each $R^1$ is independently halo, alkyl, haloalkyl, heteroalkyl, alkoxy, cyano, —$S(O)_s$—$R^c$, —C(=O)—$NR^cR^d$, —$SO_2$—$NR^cR^d$, —$N(R^c)$—C(=O)—$R^d$, or —C(=O)$R^c$, where each of $R^c$ and $R^d$ is independently hydrogen or alkyl; preferably each $R^1$ is independently halo, alkyl, or alkoxy;
s is from 0 to 2;
$R^2$ is aryl or heteroaryl; preferably $R^2$ is aryl, and more preferably optionally substituted phenyl or naphthyl such as 2-halophenyl, 3-halophenyl, 4-halophenyl, naphthylen-2-yl or 4-cyanophenyl;
each of $R^3$ and $R^4$ is independently hydrogen, alkyl, hydroxyalkyl or alkoxyalkyl, or $R^3$ and $R^4$ together with their shared carbon may form a ring of 3 to 6 members that optionally includes a nitrogen or oxygen heteroatom; and
each of $R^5$, $R^6$, $R^7$, $R^8$ and $R^9$ is independently hydrogen or alkyl, or one of $R^5$ and $R^6$ together with one of $R^7$, $R^8$ and $R^9$ together with atoms therebetween may form a ring of 5 to 7 members. Preferably $R^5$, $R^6$, $R^7$, $R^8$ and $R^9$ are hydrogen; In embodiments where any of $R^1$, $R^3$, $R^4$, $R^5$, $R^6$, $R^7$, $R^8$, $R^9$, $R^a$, $R^b$ are alkyl, they preferably are lower alkyl such as $C_1$–$C_6$alkyl, and more preferably $C_1$–$C_4$alkyl.

It is to be understood that the scope of this invention encompasses not only the various isomers which may exist but also the various mixture of isomers which may be formed. Furthermore, the scope of the present invention also encompasses solvates and salts of Compounds of Formula I.

In certain embodiments, Z is —$(CR^aR^b)_r$—, X is N, and q is 2. $R^2$ in such embodiments may comprise, for example, 2-halophenyl, 3-halophenyl, 4-halophenyl, naphthylen-2-yl, 3-cyanophenyl, 4-cyanophenyl, 3-nitrophenyl, 3-aminophenyl, 3-methoxyphenyl, 3-ureaphenyl, or 3-methylsulfonylamino-phenyl. X in many embodiments may be located at position 8 of the benzoxazinone ring system. In other embodiments X may be located at the 6-position of the benzoxazinone ring system.

In some embodiments of the invention, compounds of formula I may be of the formula II:

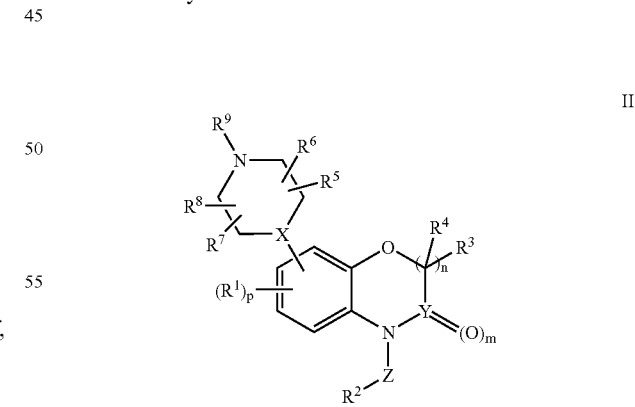

wherein X, Y, Z, $R^1$, $R^2$, $R^3$, $R^4$, $R^5$, $R^6$, $R^7$, $R^8$, $R^9$, m, n, and p are as defined herein.

In certain embodiments, compounds of formula I may be of formula III:

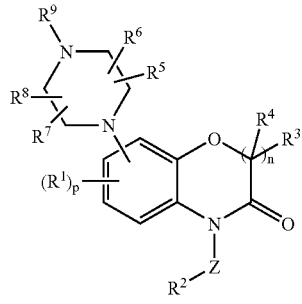

wherein X, Z, R¹, R², R³, R⁴, R⁵, R⁶, R⁷, R⁸, R⁹, n, and p are as defined herein.

In some presently preferred embodiments, compounds of formula I may be of formula IV:

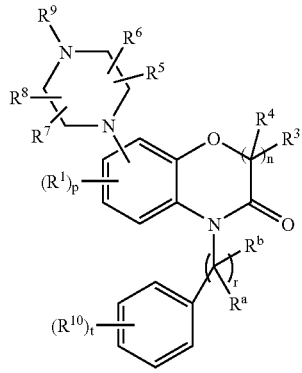

wherein R¹, R³, R⁴, R⁵, R⁶, R⁷, R⁸, R⁹, $R^a$, $R^b$ and p are as defined herein, and wherein:

t is from 0 to 4; preferably t is 1; and each $R^{10}$ independently is halo, alkyl, alkoxy, carbamyl, alkylsulfonamido, or cyano; preferably $R^{10}$ is halo or alkoxy.

In still other embodiments, the subject compounds may be of the formula V

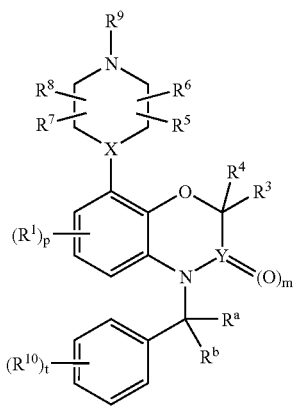

wherein X, Y, R¹, R³, R⁴, R⁵, R⁶, R⁷, R⁸, R⁹, R¹⁰, $R^a$, $R^b$, m, p and t are as defined herein. In specific embodiments of formula V, R¹ may be halo, methyl or methoxy, R³ and R⁴ may each independently be hydrogen or methyl or together with their shared carbon form a cyclobutyl group, R⁶, R⁷, R⁸, R⁹, may each independently be hydrogen or methyl, $R^a$ and $R^b$ each independently may be hydrogen or methyl, and each $R^{10}$ may be hydrogen, halo, nitro, cyano, amino, urea, methoxy or methanesulfonylamino.

Representative compounds in accordance with the invention are shown in Table 1. Melting point data in Table 1 is for the hydrochloride salts of the compounds shown unless otherwise indicated.

TABLE 1

| # | Structure | Name (AUTONOM) | MP, ° C. or M + H | Example |
|---|---|---|---|---|
| 1 | 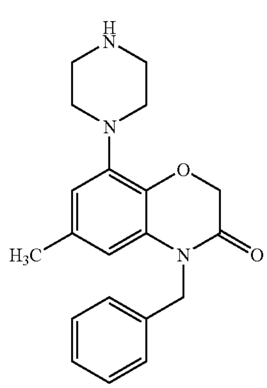 | 4-benzyl-6-methyl-8-piperazin-1-yl-4H-benzo[1,4]oxazin-3-one | 256.8–263.9 | 1 |

TABLE 1-continued

| # | Structure | Name (AUTONOM) | MP, ° C. or M + H | Example |
|---|---|---|---|---|
| 2 | 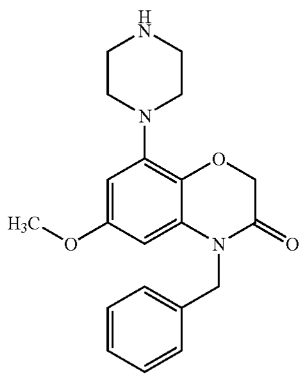 | 4-benzyl-6-methoxy-8-piperazin-1-yl-4H-benzo[1,4]oxazin-3-one | 354 | 1 |
| 3 | 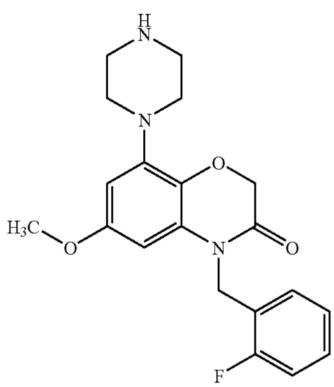 | 4-(2-fluoro-benzyl)-6-methoxy-8-piperazin-1-yl-4H-benzo[1,4]oxazin-3-one | 268.1–271.0 | 1 |
| 4 | 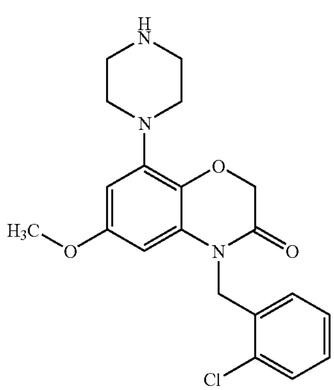 | 4-(2-chloro-benzyl)-6-methoxy-8-piperazin-1-yl-4H-benzo[1,4]oxazin-3-one | 286.9–288.9 | 1 |
| 5 | 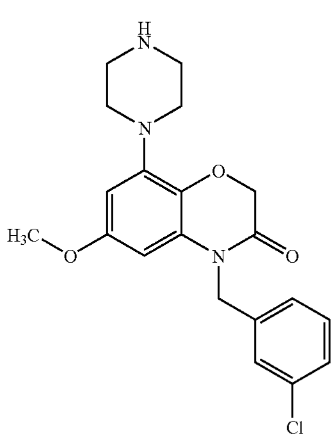 | 4-(3-chloro-benzyl)-6-methoxy-8-piperazin-1-yl-4H-benzo[1,4]oxazin-3-one | 55.2–58.8, M + H = 388 | 1 |

TABLE 1-continued
| # | Structure | Name (AUTONOM) | MP, ° C. or M + H | Example |
|---|---|---|---|---|
| 6 | 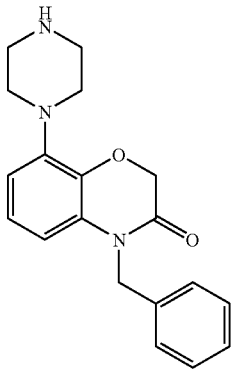 | 4-benzyl-8-piperazin-1-yl-4H-benzo[1,4]oxazin-3-one | 235.9–236.2 | 1 |
| 7 | 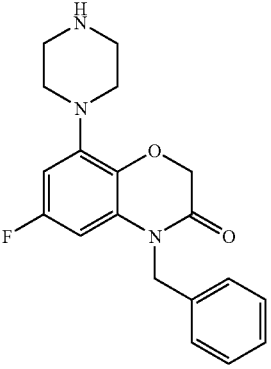 | 4-benzyl-6-fluoro-8-piperazin-1-yl-4H-benzo[1,4]oxazin-3-one | 268.2–268.3 | 1 |
| 8 | 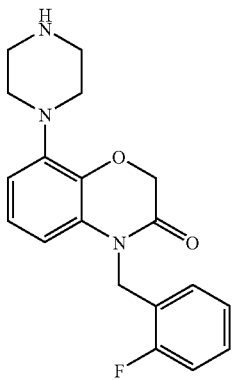 | 4-(2-fluoro-benzyl)-8-piperazin-1-yl-4H-benzo[1,4]oxazin-3-one | 236.0–244.5 | 1 |
| 9 | 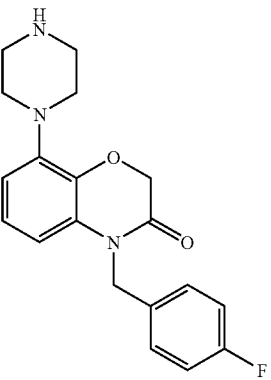 | 4-(4-fluoro-benzyl)-8-piperazin-1-yl-4H-benzo[1,4]oxazin-3-one | 240.0–242.4 | 1 |

TABLE 1-continued

| # | Structure | Name (AUTONOM) | MP, ° C. or M + H | Example |
|---|---|---|---|---|
| 10 | 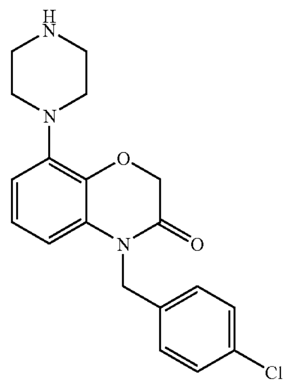 | 4-(4-chloro-benzyl)-8-piperazin-1-yl-4H-benzo[1,4]oxazin-3-one | 250.9–253.8 | 1 |
| 11 | 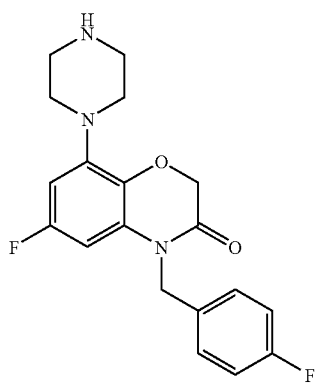 | 4-(4-fluoro-benzyl)-6-fluoro-8-piperazin-1-yl-4H-benzo[1,4]oxazin-3-one | >300 | 1 |
| 12 | 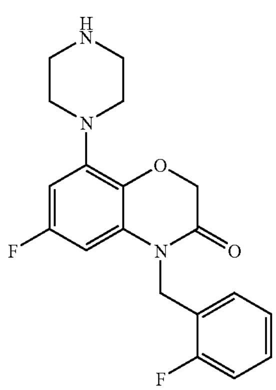 | 4-(2-fluoro-benzyl)-6-fluoro-8-piperazin-1-yl-4H-benzo[1,4]oxazin-3-one | 282.0–282.9 | 1 |
| 13 | 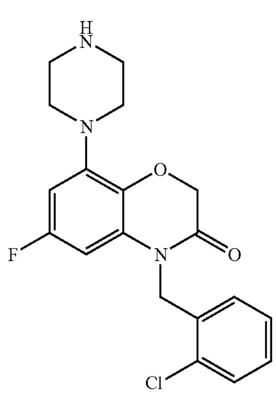 | 4-(2-chloro-benzyl)-6-fluoro-8-piperazin-1-yl-4H-benzo[1,4]oxazin-3-one | >300 | 1 |

TABLE 1-continued

| # | Structure | Name (AUTONOM) | MP, °C. or M + H | Example |
|---|---|---|---|---|
| 14 | 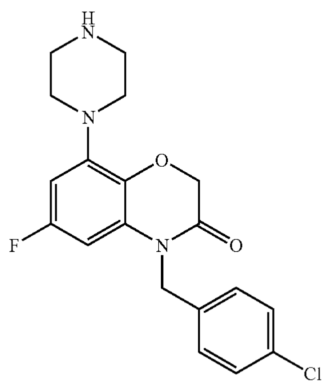 | 4-(4-chloro-benzyl)-6-fluoro-8-piperazin-1-yl-4H-benzo[1,4]oxazin-3-one | 271.7–272.4 | 1 |
| 15 | 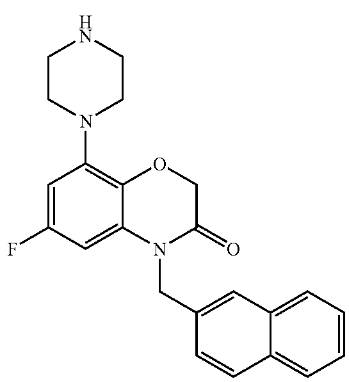 | 6-fluoro-4-naphthalen-2-ylmethyl-8-piperazin-1-yl-4H-benzo[1,4]oxazin-3-one | 255.8–256.1 | 1 |
| 16 | 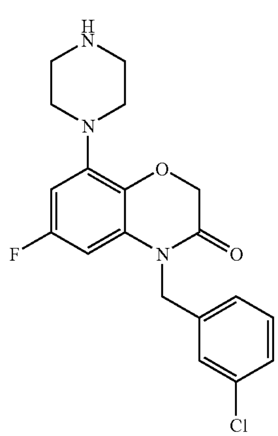 | 4-(3-chloro-benzyl)-6-fluoro-8-piperazin-1-yl-4H-benzo[1,4]oxazin-3-one | 260.2–263.1 | 1 |

TABLE 1-continued

| # | Structure | Name (AUTONOM) | MP, ° C. or M + H | Example |
|---|---|---|---|---|
| 17 | 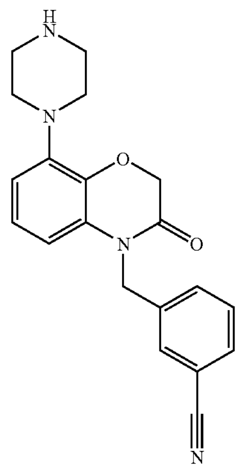 | 3-(3-Oxo-8-piperazin-1-yl-2,3-dihydro-benzo[1,4]oxazin-4-ylmethyl)-benzonitrile | 285.8–287.0 | 1 |
| 18 | 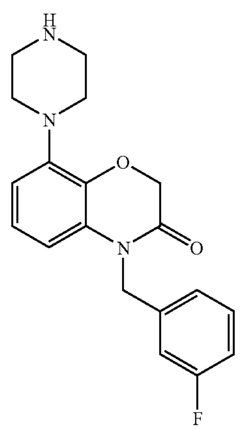 | 4-(3-fluoro-benzyl)-8-piperazin-1-yl-4H-benzo[1,4]oxazin-3-one | 231.7–236.5 | 1 |
| 19 | 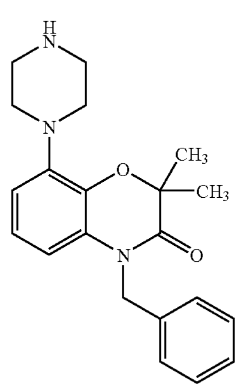 | 4-Benzyl-2,2-dimethyl-8-piperazin-1-yl-4H-benzo[1,4]oxazin-3-one | 352 | 3 |

TABLE 1-continued

| # | Structure | Name (AUTONOM) | MP, ° C. or M + H | Example |
|---|---|---|---|---|
| 20 | 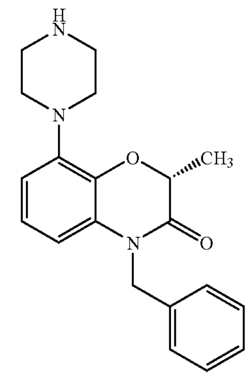 | (R)-4-Benzyl-2-methyl-8-piperazin-1-yl-4H-benzo[1,4]oxazin-3-one | 338 | 3 |
| 21 | 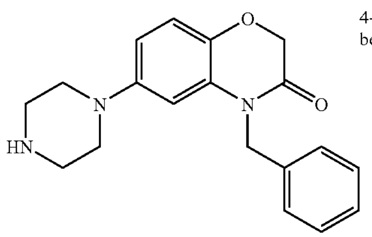 | 4-Benzyl-6-piperazin-1-yl-4H-benzo[1,4]oxazin-3-one | 324 | 1 |
| 22 | 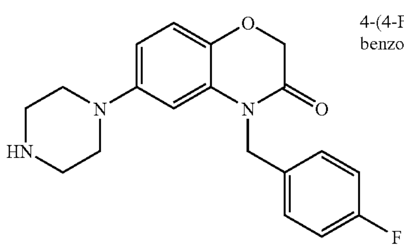 | 4-(4-Fluoro-benzyl)-6-piperazin-1-yl-4H-benzo[1,4]oxazin-3-one | 342 | 1 |
| 23 | 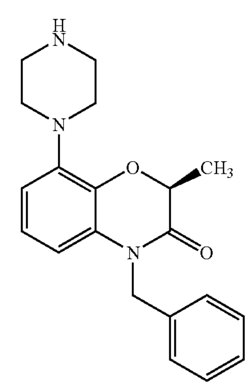 | (S)-4-Benzyl-2-methyl-8-piperazin-1-yl-4H-benzo[1,4]oxazin-3-one | 338 | 3 |

TABLE 1-continued
| # | Structure | Name (AUTONOM) | MP, ° C. or M + H | Example |
|---|---|---|---|---|
| 24 | 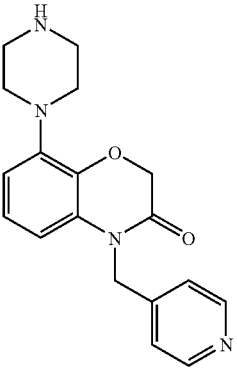 | 8-Piperazin-1-yl-4-pyridin-4-ylmethyl-4H-benzo[1,4]oxazin-3-one | 325 | 1 |
| 25 | 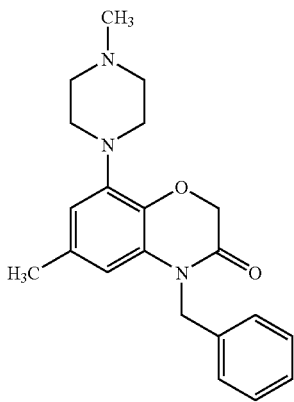 | 4-Benzyl-6-methyl-8-(4-methyl-piperazin-1-yl)-4H-benzo[1,4]oxazin-3-one | 352 | 2 |
| 26 | 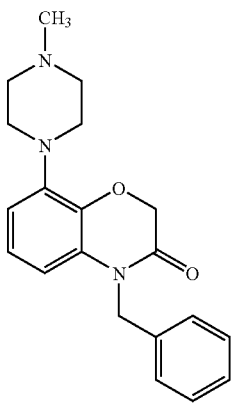 | 4-Benzyl-8-(4-methyl-piperazin-1-yl)-4H-benzo[1,4]oxazin-3-one | 338 | 2 |
| 27 | 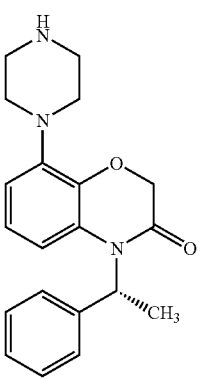 | 4-(1-Phenyl-ethyl)-8-piperazin-1-yl-4H-benzo[1,4]oxazin-3-one | 338 | 1 |

TABLE 1-continued

| # | Structure | Name (AUTONOM) | MP, ° C. or M + H | Example |
|---|---|---|---|---|
| 28 | 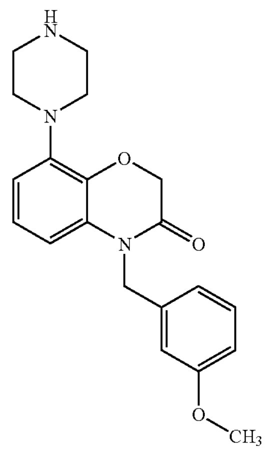 | 4-(3-Methoxy-benzyl)-8-piperazin-1-yl-4H-benzo[1,4]oxazin-3-one | 354 | 1 |
| 29 | 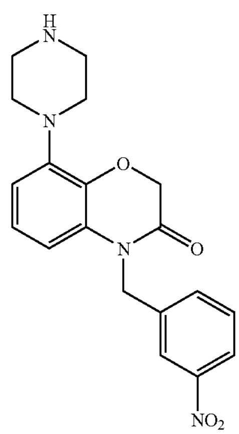 | 4-(3-Nitro-benzyl)-8-piperazin-1-yl-4H-benzo[1,4]oxazin-3-one | 369 | 1 |
| 30 | 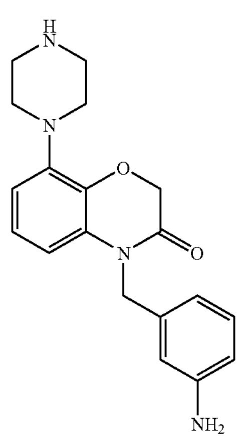 | 4-(3-Amino-benzyl)-8-piperazin-1-yl-4H-benzo[1,4]oxazin-3-one | 339 | 1 |

TABLE 1-continued

| # | Structure | Name (AUTONOM) | MP, °C. or M + H | Example |
|---|---|---|---|---|
| 31 | 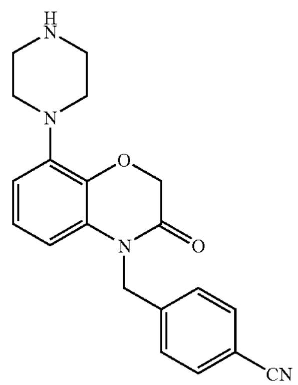 | 4-(3-Oxo-8-piperazin-1-yl-2,3-dihydro-benzo[1,4]oxazin-4-ylmethyl)-benzonitrile | 349 | 1 |
| 32 | 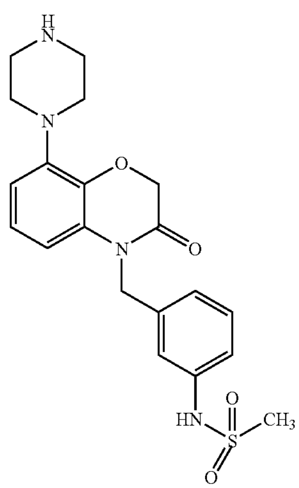 | N-[3-(3-Oxo-8-piperazin-1-yl-2,3-dihydro-benzo[1,4]oxazin-4-ylmethyl)-phenyl]-methanesulfonamide | 417 | 1 |
| 33 | 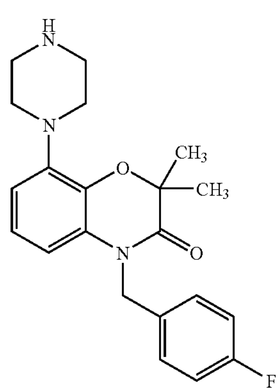 | 4-(4-Fluoro-benzyl)-2,2-dimethyl-8-piperazin-1-yl-4H-benzo[1,4]oxazin-3-one | 370 | 3 |

TABLE 1-continued

| # | Structure | Name (AUTONOM) | MP, °C. or M + H | Example |
|---|---|---|---|---|
| 34 | 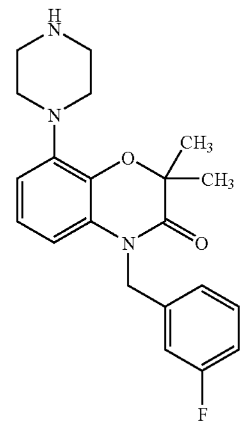 | 4-(3-Fluoro-benzyl)-2,2-dimethyl-8-piperazin-1-yl-4H-benzo[1,4]oxazin-3-one | 370 | 3 |
| 35 | 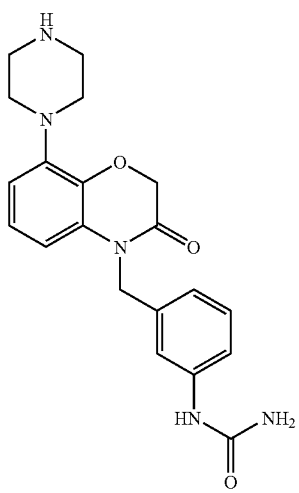 | [3-(3-Oxo-8-piperazin-1-yl-2,3-dihydro-benzo[1,4]oxazin-4-ylmethyl)-phenyl]-urea | 382 | 1 |
| 36 | 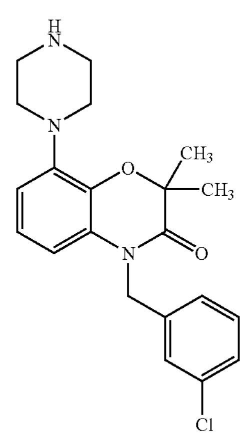 | 4-(3-Chloro-benzyl)-2,2-dimethyl-8-piperazin-1-yl-4H-benzo[1,4]oxazin-3-one | 386 | 3 |

TABLE 1-continued

| # | Structure | Name (AUTONOM) | MP, ° C. or M + H | Example |
|---|---|---|---|---|
| 37 | 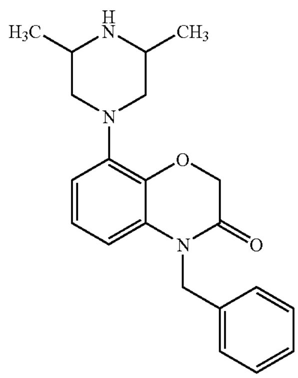 | 4-Benzyl-8-(3,5-dimethyl-piperazin-1-yl)-4H-benzo[1,4]oxazin-3-one | 352 | 1 |
| 38 | 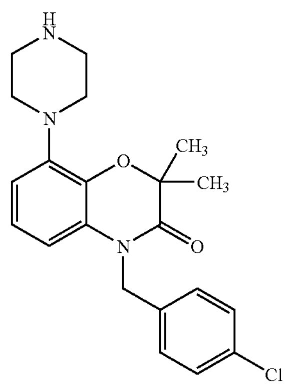 | 4-(4-Chloro-benzyl)-2,2-dimethyl-8-piperazin-1-yl-4H-benzo[1,4]oxazin-3-one | 386 | 3 |
| 39 | 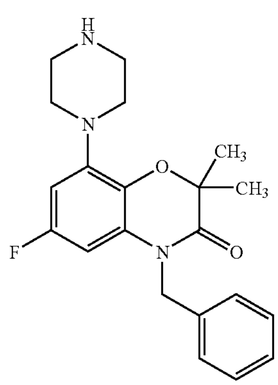 | 4-Benzyl-6-fluoro-2,2-dimethyl-8-piperazin-1-yl-4H-benzo[1,4]oxazin-3-one | 370 | 3 |
| 40 | 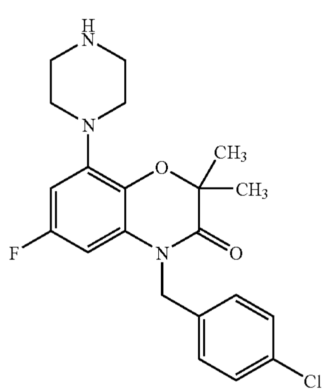 | 4-(4-Chloro-benzyl)-6-fluoro-2,2-dimethyl-8-piperazin-1-yl-4H-benzo[1,4]oxazin-3-one | 405 | 3 |

TABLE 1-continued

| # | Structure | Name (AUTONOM) | MP, ° C. or M + H | Example |
|---|---|---|---|---|
| 41 | 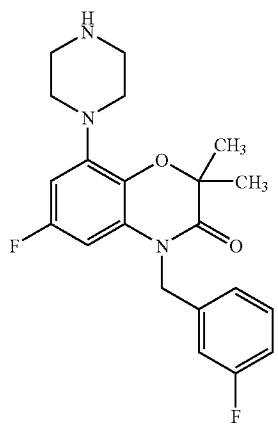 | 6-Fluoro-4-(3-fluoro-benzyl)-2,2-dimethyl-8-piperazin-1-yl-4H-benzo[1,4]oxazin-3-one | 389 | 3 |
| 42 | 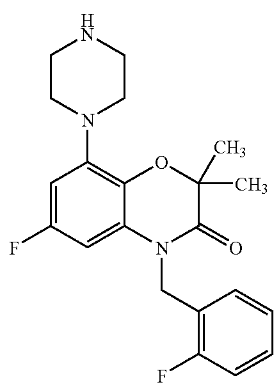 | 6-Fluoro-4-(2-fluoro-benzyl)-2,2-dimethyl-8-piperazin-1-yl-4H-benzo[1,4]oxazin-3-one | 389 | 3 |
| 43 | 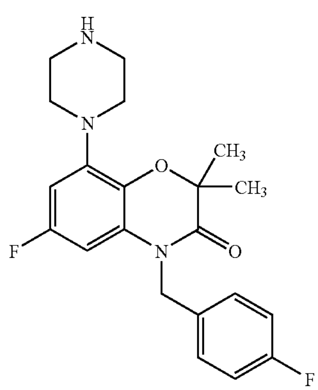 | 6-Fluoro-4-(4-fluoro-benzyl)-2,2-dimethyl-8-piperazin-1-yl-4H-benzo[1,4]oxazin-3-one | 389 | 3 |

TABLE 1-continued

| # | Structure | Name (AUTONOM) | MP, ° C. or M + H | Example |
|---|---|---|---|---|
| 44 | 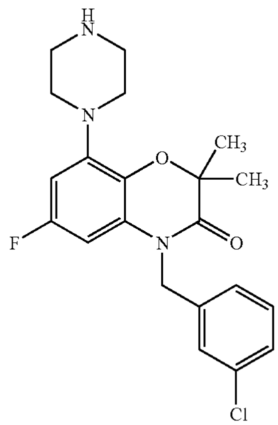 | 4-(3-Chloro-benzyl)-6-fluoro-2,2-dimethyl-8-piperazin-1-yl-4H-benzo[1,4]oxazin-3-one | 405 | 3 |
| 45 | 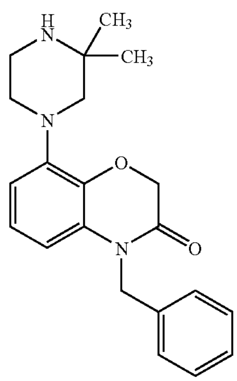 | 4-Benzyl-8-(3,3-dimethyl-piperazin-1-yl)-4H-benzo[1,4]oxazin-3-one | 352 | 1 |
| 46 | 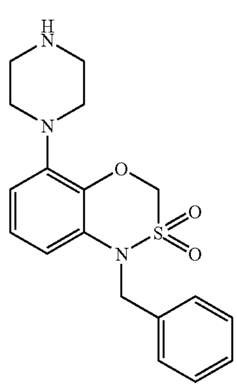 | 1-Benzyl-5-piperazin-1-yl-1H-benzo[1,3,4]oxathiazine 2,2-dioxide | 360 | 4 |

TABLE 1-continued

| # | Structure | Name (AUTONOM) | MP, ° C. or M + H | Example |
|---|---|---|---|---|
| 47 | 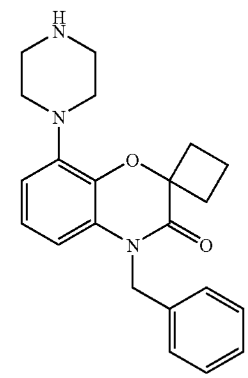 | 4-Benzyl-2,2-spiro-cyclobutan-8-piperazin-1-yl-4H-benzo[1,4]oxazin-3-one hydrochloride salt | 363 | 3 |

Another aspect of the invention provides a composition comprising a therapeutically effective amount of at least one compound of formula I and a pharmaceutically acceptable carrier.

Yet another aspect of the invention provides a method for treating a central nervous system (CNS) disease state in a subject comprising administering to the subject a therapeutically effective amount of a compound of formula I. The disease state may comprise, for example, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a Compound of Formula I.

Another aspect of the present invention provides a method for producing a compound of formula I.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates the synthetic procedure usable to prepare specific compounds of Formula I wherein each A independently is halo or other leaving group (such as triflate) and may be the same or different in each occurrence, and $R^1$, $R^2$, $R^3$, $R^4$, $R^5$, $R^6$, $R^7$, $R^8$, $R^9$, $R^{10}$, $R^a$, $R^b$, n, p, q, r and t are as defined herein.

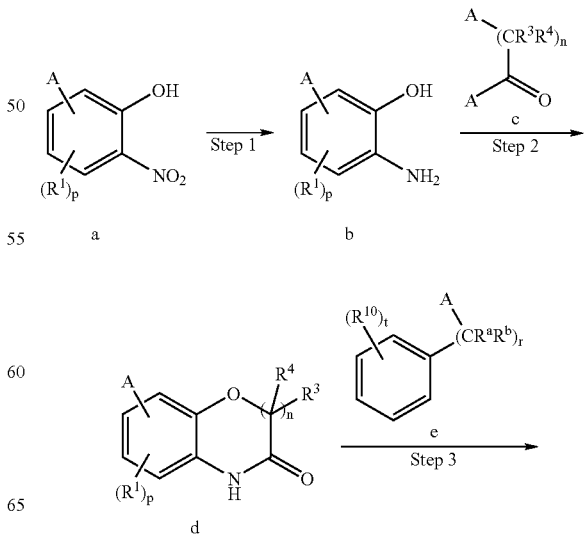

SCHEME A

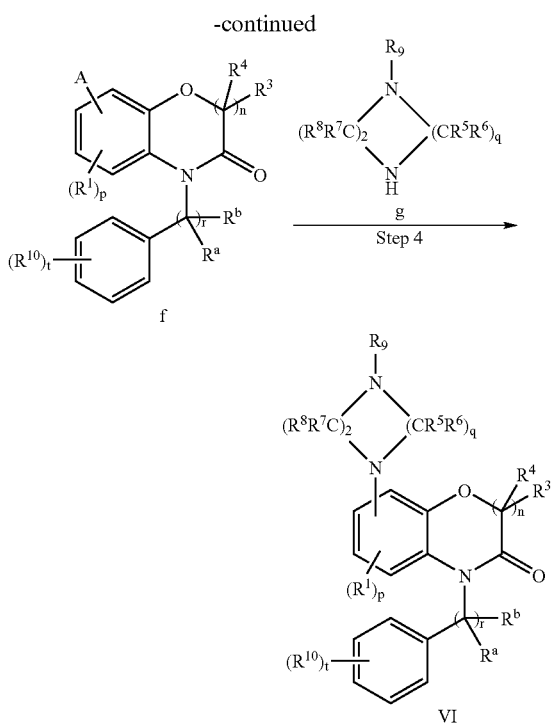

In Step 1 of Scheme A, an ortho nitrophenol a is reduced to the corresponding aniline or aminophenol b. This reduction may be carried out under relatively mild, aqueous conditions, using sodium dithionite or like mild reducing agent.

A cyclization is then carried out in Step 2 to provide the benzoxazinone compound d from the aminophenol b generated in Step 1. Where n is 1, for example, the benzoxazinone d is a 2H-1,4-benzoxazin-3(4H)-one, and where n is 2 the compound d is a 2,3-Dihydro-1,5-benzoxazepin-4(5H)-one. The cyclization may be achieved by reaction of the aminophenol b with a 2-halo acid halide c such as chloroacetyl chloride (to provide n=1 and $R^3$, $R^4$ as hydrogen), 2-chloropropionyl chloride (which provides n=1, $R^3$ as methyl and $R^4$ as hydrogen), 3-chloropropionyl chloride (providing n=2 and $R^3$, $R^4$ as hydrogen), 2-chloroisobutyryl chloride (providing n=1, $R^3$ as isopropyl and $R^4$ as hydrogen), 2-chloro-2-methylpropionyl chloride (providing n=1 and $R^3$ and $R^4$ as methyl), and so on. Formation of benzoxazinones in this manner can be achieved under relatively mild polar conditions in the presence of a mild base, as described by Combs et al.; J. Med. Chem.; 33; 380–386 1990. The cyclization may also be achieved by reacting b with a 2-hydroxyester under Mitsunobu reaction conditions, as described by Van Hes et al in WO 01/14330.

In Step 3, an N-alkylation of the benzoxazinone compound d is carried out by treatment of compound d from Step 2 with a strong base under dry, polar aprotic conditions and reaction with an α-haloalkyl aryl compound e to provide the N-arylalkyl-benzoxazinone compound f. The haloalkyl aryl compound e may comprise, for example, benzyl halide (to provide r=1 and $R^a$ and $R^b$ as hydrogen), 3-halo-3-phenylpropane (providing r=2 and $R^a$, $R^b$ as hydrogen), α-methylbenzyl halide (providing r=1, $R^a$ as hydrogen and $R^b$ as methyl), or other α-haloalkylphenyl halides according to the desired $R^a$ and $R^b$ substituent configuration.

The alkylation of Step 3 may also be carried out using α-haloalkyl napthyl compounds, α-haloalkylbiphenyl compounds or other α-haloalkylaryl compounds. In other embodiments Step 3 may be carried out using α-haloalkyl heteroaryl compounds such as α-haloalkylpyridines, α-haloalkylthiophenes, α-haloalkylmethylenedioxyphenyl compounds, α-haloalkylethylenedioxyphenyl compounds, and the like. In the case of α-haloalkyl heteroaryl compounds, suitable protection group strategies may be employed to avoid unwanted heteroatom alkylation during this step. In certain embodiments, the alkylation of Step 3 may be replaced by an aryl- or heteroaryl-sulfonylation wherein a suitable arylsulfonyl halide or heteroarylsulfonyl halide is reacted with the ring nitrogen of the benzoxazinone compound d.

An amination reaction is then carried out in Step 4 wherein the N-arylalkyl-benzoxazinone compound e is reacted with a nitrogen-containing heterocycle f in the presence of a palladium catalyst to replace the leaving group A- with a heterocyclyl group and provide the heterocyclyl-N-arylalkyl-benzoxazinone compound VI. In many embodiments q is 1 such that the heterocycle compound f is a piperazine compound of the formula h:

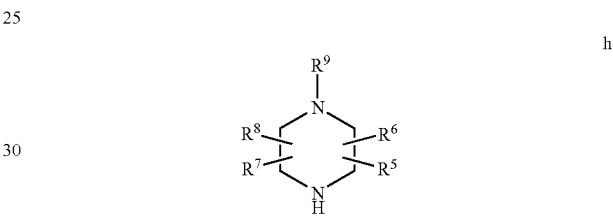

and such that the heterocyclyl-N-arylalkyl-benzoxazinone compound VI is of the formula IV:

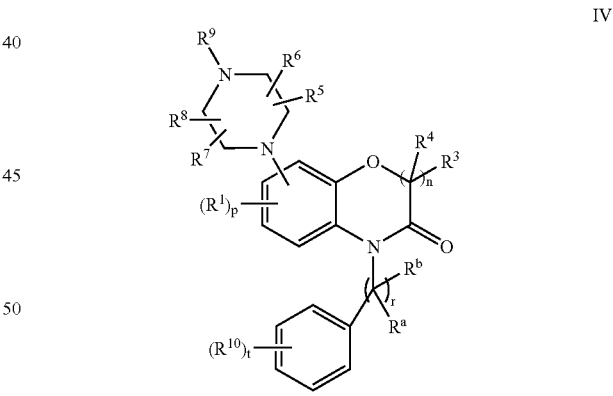

which is discussed above. Several alkyl-substituted piperazine compounds are commercially available or easily prepared according to known procedures and may be used in this step. The amination of Step 4 may be effected at both the 8- and 6-positions under similar reaction conditions.

In instances where $R^9$ is hydrogen, BOC protection or other suitable protection strategies may be used to protect the corresponding ring nitrogen of compound f. Where a BOC protection group is present, deprotection may be carried out in this step by treatment of the heterocyclyl-N-arylalkyl-benzoxazinone compound V with mild acid solution.

Many variations on the above procedure may suggest themselves to those skilled in the art upon review of this disclosure. In some instances, amination may be carried out prior to N-alkylation at the 1-position. The number, functionality and/or location of the $R^1$ substituent groups may be selected to activate particular positions (i.e., any of positions 5 through 8) of the benzoxazinone ring and thus facilitate amination at selected positions as desired for specific embodiments of the subject compounds.

More specific details for producing Compounds of Formula I are described in the Examples section below.

Utility

The compounds of the invention have selective affinity for 5-HT receptors, including 5-HT$_6$, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor in radioligand binding and functional assays are described in Example 4.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multidose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 6–12.

EXAMPLES

The following preparations and examples are given to enable those skilled in the art to more clearly understand and to practice the present invention. They should not be considered as limiting the scope of the invention, but merely as being illustrative and representative thereof.

Example 1

4-benzyl-8-piperazin-1-yl-4H-benzo[1,4]oxazin-3-one hydrochloride salt

The synthetic procedures described in this Example were carried out according to the process shown in Scheme B wherein $R^1$ and $R^{10}$ are as defined herein.

SCHEME B

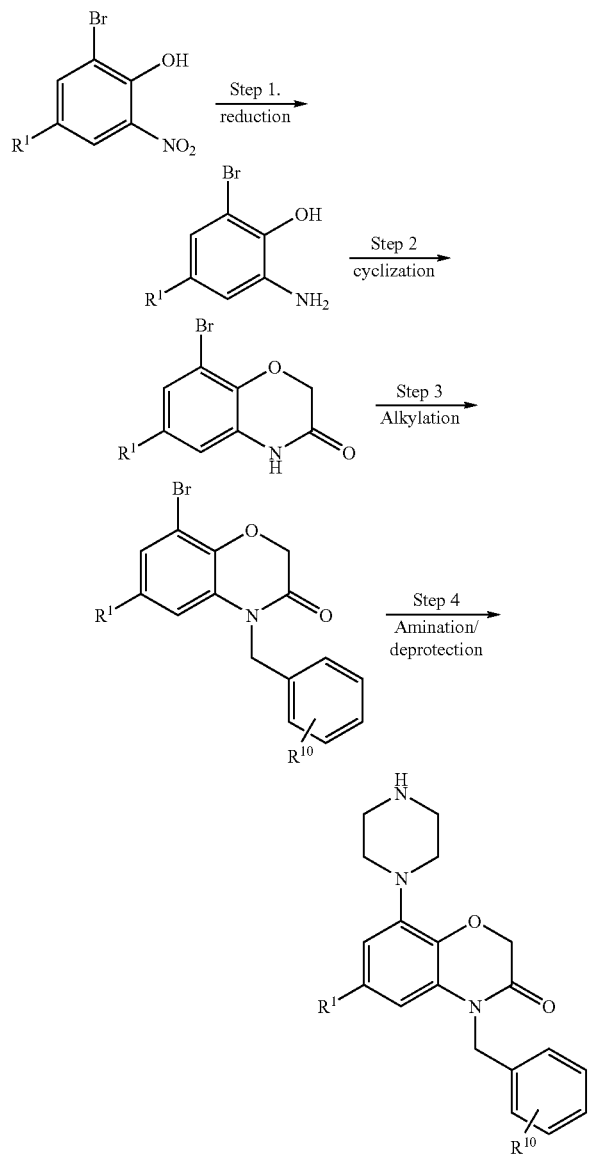

Step 1:

2-amino-6-bromo-4-fluorophenol

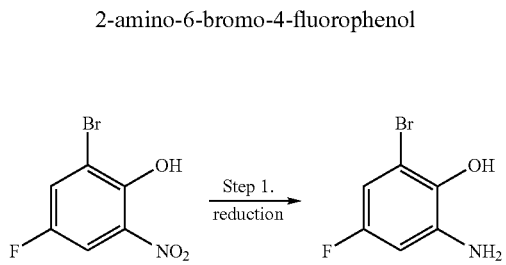

Sodium dithionite (58 g, 335 mmol) was dissolved in warm water (300 mL) and was added slowly to a solution of 6-bromo-4-fluoro-2-nitrophenol (11.8 g, 50 mmol) in 250 mL of ethanol heated on a steam bath. The reaction mixture turned from deep orange to light yellow. The suspension is diluted with water till a clear yellow solution was obtained. Partial concentration on a rotary evaporator induced crystallization. The mixture was then cooled to room temperature and crystals formed. Filtration and drying afforded the title compound as a white solid (5.04 g, 49% yield). MS 207 $(M+H)^+$ Step 2:

8-bromo-6-methoxy-4H-benzo[1,4]oxazin-3-one

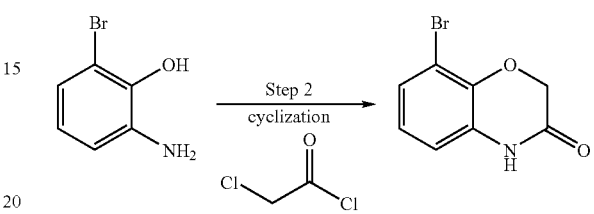

The reaction in this Example was carried out following similar procedures reported in literature. See for example, Combs, Donald W.; Rampulla, Marianne S.; Bell, Stanley C.; Klaubert, Dieter H.; Tobia, Alfonso J.; et al.; J. Med. Chem.; 33; 1990; 380–386.

A saturated solution of $NaHCO_3$ in water (20 mL) was added to a solution of 2-amino-6-bromo-4-methoxyphenol (9.8 g, 45 mmol) in 300 mL of 2-butanone. Chloroacetyl chloride (6.1 g, 54 mmol) was added dropwise at room temperature, and the mixture was brought to reflux while stirring for 2 hours. After cooling to room temperature, water and ethyl acetate were added and organic layer was separated and dried over $Na_2SO_4$, filtered, concentrated to give a light brown solid. Recrystallization from EtOAc gave 2.2 g of the title compound as light red solids. The mother liquor was chromatographed on silica gel using EtOAc/Hex (1:4) to give another 2.6 g of light red solids. MP=236.1–237.5° C.

The following compounds were prepared in a similar manner:
8-bromo-4H-benzo[1,4]oxazin-3-one, MP=243.5–244.9° C.
8-bromo-6-fluoro-4H-benzo[1,4]oxazin-3-one, MS 247 $(M+H)^+$ Step 3:

4-Benzyl-8-bromo-4H-benzo[1,4]oxazin-3-one

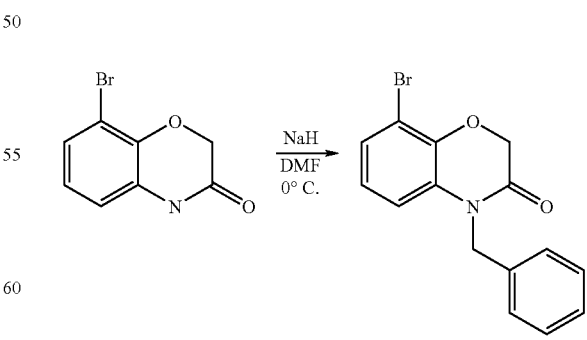

To a solution of 8-bromo-4H-benzo[1,4]oxazin-3-one (343 mg, 1.5 mmol) in 10 ml anhydrous dimethylformanide was added sodium hydride (120 mg of a 60% suspension in mineral oil, 3.0 mmol) portionwise at 0° C. The solution was stirred with a magnetic stirrer at 0° C. for 20 minutes, at which time the initial gas evolution ended. Benzyl bromide (0.22 ml, 1.8 mmol) was added in one portion and the reaction mixture was stirred at 0° C. for 30 minutes. The solution was allowed to warm to room temperature and the reaction mixture was partitioned between water (50 ml) and ethyl acetate (50 ml). The aqueous layer was extracted with ethyl acetate (2×25 ml) and the combined organic fractions were washed with water (2×25 ml) and brine (2×25 ml). After drying over MgSO₄, the organic fraction was concentrated in vacuo and resulting brown residue was purified by flash chromatography (5%–15% Ethyl acetate/Hexane in 30 minutes) to give 402 mg of 4-benzyl-8-bromo-4H-benzo[1,4]oxazin-3-one as a yellow solid (84%). MS: 318 (M+H)⁺.

The following compounds were prepared in a similar fashion starting with appropriate bromobenzo[1,4]oxazinone and various arylalkyl bromides and arylalkyl chlorides, which are either commercially available or known in the literature:

4-Benzyl-8-bromo-6-methyl-4H-benzo[1,4]oxazin-3-one, MS (M+H)⁺: 334.0.

4-Benzyl-8-bromo-6-methoxy-4H-benzo[1,4]oxazin-3-one, MS (M+H)⁺: 350.0.

8-Bromo-4-(2-fluoro-benzyl)-6-methoxy-4H-benzo[1,4]oxazin-3-one, MS (M+H)⁺: 367.9.

8-Bromo-4-(2-chloro-benzyl)-6-methoxy-4H-benzo[1,4]oxazin-3-one, ¹H NMR (CDCl₃, 300 MHz) δ: 3.66 (s, 3H), 4.79 (s, 2H), 5.22 (s, 2H), 6.29 (d, 1H, J=2.83 Hz), 6.74 (d, 1H, J=2.83 Hz), 7.00 (m, 1H), 7.20 (m, 2H), 7.42 (m, 1H).

8-Bromo-4-(3-chloro-benzyl)-6-methoxy-4H-benzo[1,4]oxazin-3-one, MS (M+H)⁺: 382.9

4-Benzyl-8-bromo-6-fluoro-4H-benzo[1,4]oxazin-3-one, MS (M+H)⁺: 335.0

8-Bromo-4-(2-fluoro-benzyl)-4H-benzo[1,4]oxazin-3-one, MS (M+H)⁺: 338.1

8-Bromo-4-(4-fluoro-benzyl)-4H-benzo[1,4]oxazin-3-one, MS (M+H)⁺: 334.9

8-Bromo-4-(4-chloro-benzyl)-4H-benzo[1,4]oxazin-3-one, MS (M+H)⁺: 354.0

8-Bromo-6-fluoro-4-(4-fluoro-benzyl)-4H-benzo[1,4]oxazin-3-one, MS (M+H)⁺: 352.9

8-Bromo-6-fluoro-4-(2-fluoro-benzyl)-4H-benzo[1,4]oxazin-3-one, ¹H NMR (CDCl₃, 300 MHz) δ: 4.79 (s, 2H), 5.18 (s, 2H), 6.63 (dd, 1H, J=2.64 Hz, 9.42 Hz), 6.96 (dd, 1H, J=2.83 Hz, 7.73 Hz), 7.10 (m, 3H), 7.28 (m, 1H).

8-Bromo-6-fluoro-4-(2-chloro-benzyl)-4H-benzo[1,4]oxazin-3-one, MS (M+H)⁺: 371.0

8-Bromo-6-fluoro-4-(4-chloro-benzyl)-4H-benzo[1,4]oxazin-3-one, MS (M+H)⁺: 370.9

8-Bromo-6-fluoro-4-naphthalen-2-ylmethyl-4H-benzo[1,4]oxazin-3-one, MS (M+H)⁺: 384.9

Step 4:

4-benzyl-8-piperazin-1-yl-4H-benzo[1,4]oxazin-3-one Hydrochloride Salt

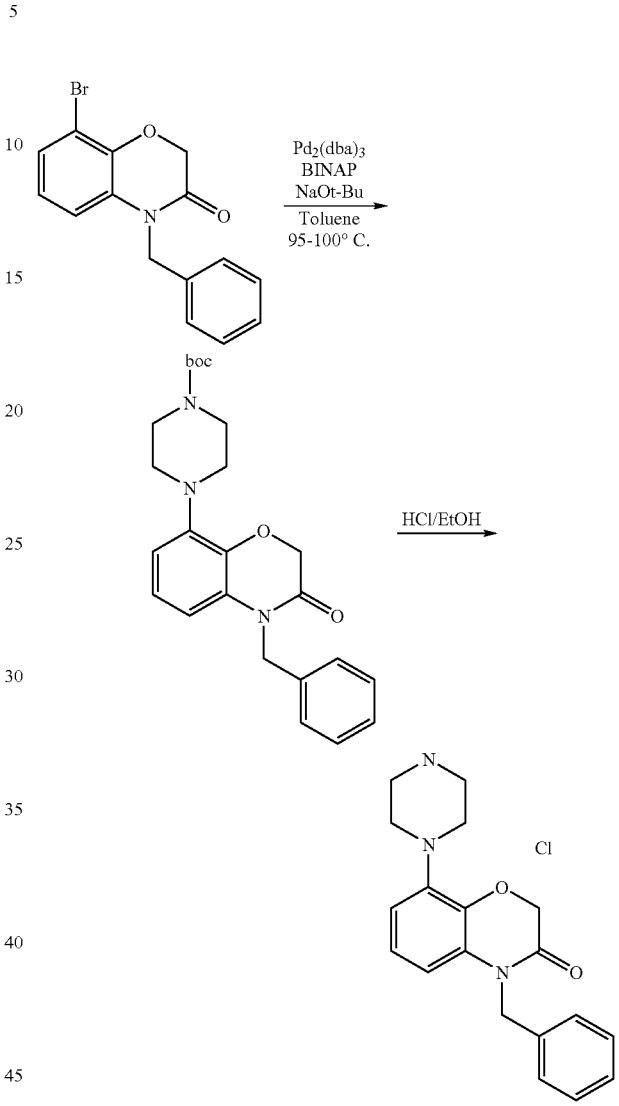

A solution of 4-benzyl-8-bromo-4H-benzo[1,4]oxazin-3-one (402 mg, 1.26 mmol) and 1-Boc-piperazine (285 mg, 1.53 mmol) in 3 mL of toluene was added to the mixture of Pd₂(dba)₃ (28 mg, 0.03 mmol), BINAP (2,2'-bis(diphenylphosphino)-1,1'-binaphthyl) (41 mg, 0.066 mmol), NaOt-Bu (175 mg, 1.82 mmol). With stirring, the solution was heated at 95° C.–100° C. for 1 hour and was allowed to cool to room temperature. The reaction mixture was filtered through celite and washed with ethyl acetate. The filtrate was washed with water (2×15 ml) and brine (1×15 ml). After drying over MgSO₄, the organic fraction was concentrated in vacuo and resulting brown residue was purified by flash chromatography (10%–40% Ethyl acetate/Hexane in 30 minutes) to give 168 mg of the boc-protected compound as a yellow solid (32%). 4-(4-Benzyl-3-oxo-3,4-dihydro-2H-benzo[1,4]oxazin-8-yl)-piperazine-1-carboxylic acid tert-butyl ester (0.168 g., 0.4 mmol) was dissolved in 4 ml ethanol. To this solution was added 2 M ethanolic hydrochloric acid solution (3 ml.). The mixture was heated at 100° C. (steam bath) for 20 minutes, at which time crystalline solids formed. The solution was allowed to cool to room temperature and 0.115 g. of 4-benzyl-8-piperazin-1-yl-4H-benzo[1,4]oxazin-3-one hydrochloride salt is collected as a light yellow powder after filtering and drying in a vacuum oven. MS: 324 (M+H)$^+$, mp=235.9–236.2° C.

The following compounds were prepared in a similar fashion starting with appropriate substituted bromobenzo[1,4]oxazinones:

4-benzyl-6-methyl-8-piperazin-1-yl-4H-benzo[1,4]oxazin-3-one hydrochloride salt, MS: (M+H)$^+$338, mp=256.8–263.9° C.

4-benzyl-6-methoxy-8-piperazin-1-yl-4H-benzo[1,4]oxazin-3-one hydrochloride salt, MS: (M+H)$^+$354.

4-(2-fluoro-benzyl)-6-methoxy-8-piperazin-1-yl-4H-benzo[1,4]oxazin-3-one hydrochloride salt, MS: (M+H)$^+$372, mp=268.1–271.0° C.

4-(2-chloro-benzyl)-6-methoxy-8-piperazin-1-yl-4H-benzo[1,4]oxazin-3-one hydrochloride salt, MS: (M+H)$^+$388, mp=286.9–288.9° C.

4-(3-chloro-benzyl)-6-methoxy-8-piperazin-1-yl-4H-benzo[1,4]oxazin-3-one hydrochloride salt, MS: (M+H)$^+$388, mp=55.2–58.8° C.

4-benzyl-6-fluoro-8-piperazin-1-yl-4H-benzo[1,4]oxazin-3-one hydrochloride salt, MS: (M+H)$^+$342, mp=268.2–268.3° C.

4-(2-fluoro-benzyl)-8-piperazin-1-yl-4H-benzo[1,4]oxazin-3-one hydrochloride salt, MS: (M+H)$^+$342, mp=236.0–244.5° C.

4-(3-fluoro-benzyl)-8-piperazin-1-yl-4H-benzo[1,4]oxazin-3-one hydrochloride salt, mp=231.7–236.5° C.

4-(4-fluoro-benzyl)-8-piperazin-1-yl-4H-benzo[1,4]oxazin-3-one hydrochloride salt, MS: (M+H)$^+$342, mp=240.0–242.4° C.

4-(4-chloro-benzyl)-8-piperazin-1-yl-4H-benzo[1,4]oxazin-3-one hydrochloride salt, MS: (M+H)$^+$358, mp=250.9–253.8° C.

4-(4-fluoro-benzyl)-6-fluoro-8-piperazin-1-yl-4H-benzo[1,4]oxazin-3-one hydrochloride salt, MS: (M+H)$^+$360, mp=>300° C.

4-(2-fluoro-benzyl)-6-fluoro-8-piperazin-1-yl-4H-benzo[1,4]oxazin-3-one hydrochloride salt, MS: (M+H)$^+$360, mp=282.0–282.9° C.

4-(2-chloro-benzyl)-6-fluoro-8-piperazin-1-yl-4H-benzo[1,4]oxazin-3-one hydrochloride salt, MS: (M+H)$^+$376, mp=>300° C.

4-(4-chloro-benzyl)-6-fluoro-8-piperazin-1-yl-4H-benzo[1,4]oxazin-3-one hydrochloride salt, MS: (M+H)$^+$376, mp=271.7–272.4° C.

6-fluoro-4-naphthalen-2-ylmethyl-8-piperazin-1-yl-4H-benzo[1,4]oxazin-3-one hydrochloride salt, MS: (M+H)$^+$ 392, mp=255.8–256.1° C.

4-(3-Methoxy-benzyl)-8-piperazin-1-yl-4H-benzo[1,4]oxazin-3-one, hydrochloride salt. MS: (M+H)$^+$354.

4-(3-Nitro-benzyl)-8-piperazin-1-yl-4H-benzo[1,4]oxazin-3-one, hydrochloride salt. MS: (M+H)$^+$369.

4-(3-Amino-benzyl)-8-piperazin-1-yl-4H-benzo[1,4]oxazin-3-one, hydrochloride salt. MS: (M+H)$^+$339.

3-(3-Oxo-8-piperazin-1-yl-2,3-dihydro-benzo[1,4]oxazin-4-ylmethyl)-benzonitrile, hydrochloride salt. MS: (M+H)$^+$349.

4-(3-Oxo-8-piperazin-1-yl-2,3-dihydro-benzo[1,4]oxazin-4-ylmethyl)-benzonitrile, hydrochloride salt. MS: (M+H)$^+$349.

N-[3-(3-Oxo-8-piperazin-1-yl-2,3-dihydro-benzo[1,4]oxazin-4-ylmethyl)-phenyl]methanesulfonamide, hydrochloride salt. MS: (M+H)$^+$417.

[3-(3-Oxo-8-piperazin-1-yl-2,3-dihydro-benzo[1,4]oxazin-4-ylmethyl)-phenyl]-urea, hydrochloride salt. MS: (M+H)$^+$382.

4-(3-chloro-benzyl)-6-fluoro-8-piperazin-1-yl-4H-benzo[1,4]oxazin-3-one, hydrochloride salt. mp=260.2–263.1° C.

Using the above procedure, but with 4-bromomethyl pyridine in step 3 instead of benzyl bromide, 8-Piperazin-1-yl-4-pyridin-4-ylmethyl-4H-benzo[1,4]oxazin-3-one, hydrochloride salt was prepared. MS: (M+H)$^+$325.

Using the above procedure, but with 1-bromoethyl benzene in step 3 instead of benzyl bromide, 4-(1-Phenyl-ethyl)-8-piperazin-1-yl-4H-benzo[1,4]oxazin-3-one, hydrochloride salt was prepared. MS: (M+H)$^+$338.

Using the above procedure, but in step 4 replacing the boc-protected piperazine with boc protected 3,5-dimethyl-piperazine afforded 4-Benzyl-8-(3,5-dimethyl-piperazin-1-yl)-4H-benzo[1,4]oxazin-3-one, hydrochloride salt. MS: (M+H)$^+$352. Similarly, using boc-protected 3,3-dimethyl-piperazine in step 4 provided 4-Benzyl-8-(3,3-dimethyl-piperazin-1-yl)-4H-benzo[1,4]oxazin-3-one, hydrochloride salt. MS: (M+H)$^+$352.

Similarly, but using 2-amino-6-bromo-4-methoxyphenol in step 2 to provide 6-bromo-4H-benzo[1,4]oxazin-3-one in step 3, the following compounds were prepared:

4-Benzyl-6-piperazin-1-yl-4H-benzo[1,4]oxazin-3-one, hydrochloride salt. MS: (M+H)$^+$324.

4-(4-Fluoro-benzyl)-6-piperazin-1-yl-4H-benzo[1,4]oxazin-3-one, hydrochloride salt, MS: (M+H)$^+$342.

Example 2

4-Benzyl-6-methyl-8-(4-methyl-piperazin-1-yl)-4H-benzo[1,4]oxazin-3-one

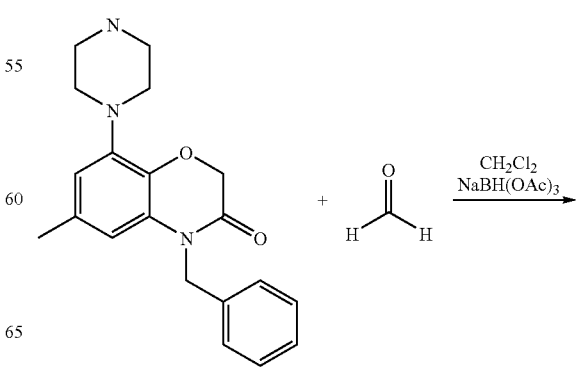

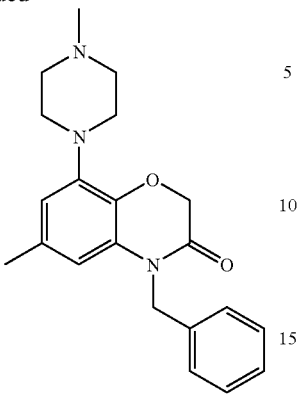

To a solution of 4-Benzyl-6-methyl-8-piperazin-1-yl-4H-benzo[1,4]oxazin-3-one (140 mg, 0.42 mmol) in CH$_2$Cl$_2$ (5 ml) from Example 1 was added formaldehyde (37 wt % solution in water, 50 µl, 0.67 mmol) and NaBH(OAc)$_3$. The solution was stirred with a magnetic stirrer at room temperature for 2 hours, and then partitioned between CH$_2$Cl$_2$ (20 ml) and saturated NaHCO$_3$ solution (20 ml). The aqueous layer was extracted with CH$_2$Cl$_2$ (2×20 ml). After drying over MgSO$_4$, the organic fraction was concentrated in vacuo to give 4-Benzyl-6-methyl-8-(4-methyl-piperazin-1-yl)-4H-benzo[1,4]oxazin-3-one as yellow solid. (140 mg, 95%) MS: (M+H)$^+$352.

Similarly prepared from 4-benzyl-8-piperazin-1-yl-4H-benzo[1,4]oxazin-3-one was 4-Benzyl-8-(4-methyl-piperazin-1-yl)-4H-benzo[1,4]oxazin-3-one: MS: (M+H)$^+$338.

Example 3

4-Benzyl-2,2-dimethyl-8-piperazin-1-yl-4H-benzo[1,4]oxazin-3-one

The synthetic procedures described in this Example were carried out according to the process shown in Scheme C wherein R$^1$ and R$^{10}$ are as defined herein.

SCHEME C

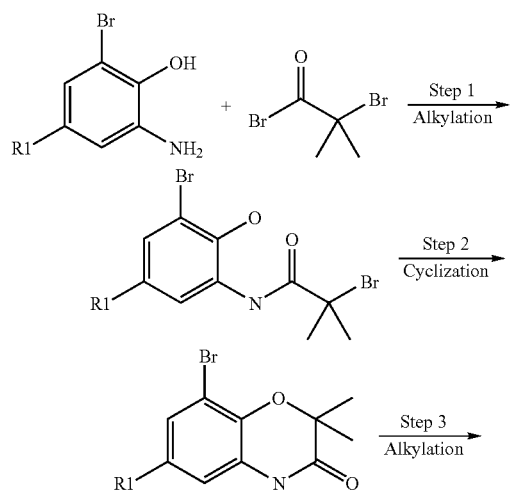

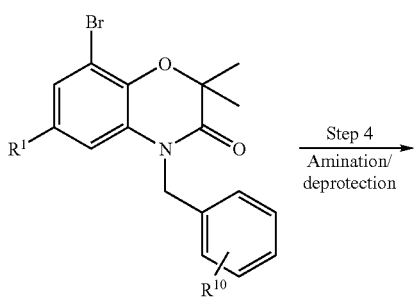

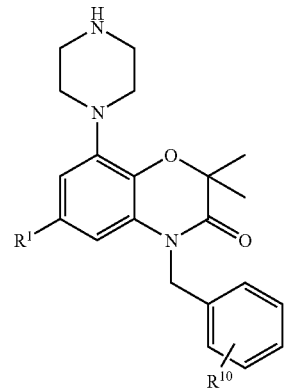

Step 1

2-Bromo-N-(3-bromo-2-hydroxy-phenyl)-2-methyl-propionamide

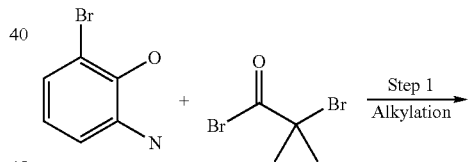

Pyridine (1.8 ml, 22.3 mmol) was added to a solution of 2-Amino-6-bromo-phenol (4.198 g, 22.3 mmol) in dry CH$_2$Cl$_2$ (200 ml). The mixture was cooled in ice and then a solution of 2-bromo-2-methyl-propionylbromide (2.8 ml, 22.6 mmol) was added slowly. The mixture was stirred at the room temperature for an hour and was poured into CH$_2$Cl$_2$ and water. The organic layer was washed with water, dried and concentrated in vacuo to yield crude 2-bromo-N-(3-bromo-2-hydroxy-phenyl)-2-methyl-propionamide, which was used directly in step 2.

Step 2

8-Bromo-2,2-dimethyl-4H-benzo[1,4]oxazin-3-one

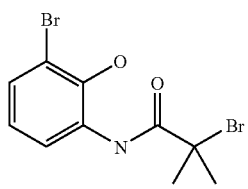

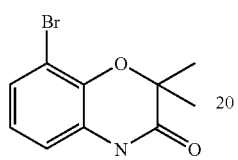

The 2-bromo-N-(3-bromo-2-hydroxy-phenyl)-2-methyl-propionamide of step 1 was dissolved in DMF (200 ml), and the DMF solution was added to K$_2$CO$_3$ (6.3 g, 45.58 mmol). The mixture was heated overnight at 150° C., then cooled and poured into a mixture of water/ethyl acetate. The organic fraction was washed with brine. After drying over MgSO$_4$, the organic fraction was concentrated in vacuo and resulting brown residue was purified by flash chromatography to give 8-Bromo-2,2-dimethyl-4H-benzo[1,4]oxazin-3-one as a white solid (84.6%). MS: (M−H)⁻256.

Similarly prepared was 8-bromo-6-fluoro-2,2-dimethyl-4H-benzo[1,4]oxazin-3-one: MS: (M−H)⁻272.

Step 3

4-Benzyl-8-bromo-2,2-dimethyl-4H-benzo[1,4]oxazin-3-one

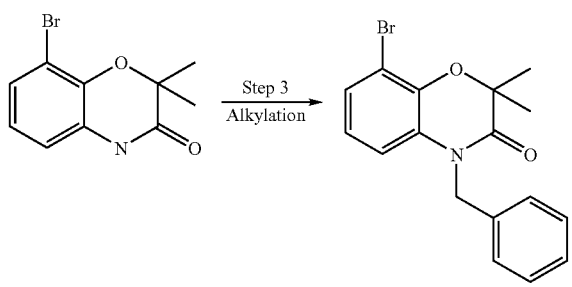

The N-benzylation of 8-bromo-2,2-dimethyl-4H-benzo[1,4]oxazin-3-one in this step was carried out using the procedure of Step 3 of Example 1 as described above, to afford 4-benzyl-8-bromo-2,2-dimethyl-4H-benzo[1,4]oxazin-3-one. MS: (M+H) 347.

Step 4

4-Benzyl-2,2-dimethyl-8-piperazin-1-yl-4H-benzo[1,4]oxazin-3-one

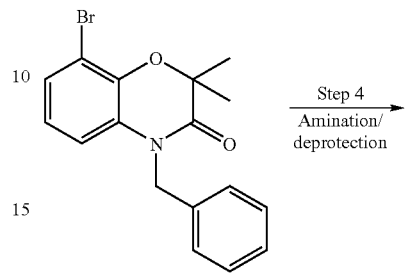

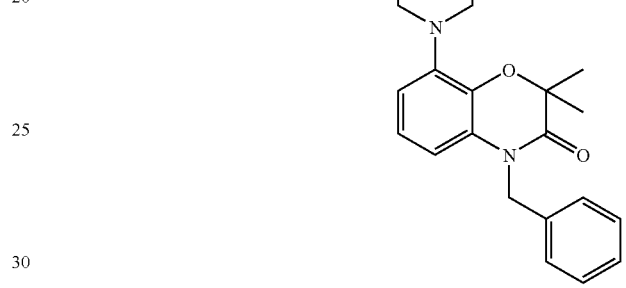

The amination and subsequent deprotection of 4-benzyl-8-bromo-2,2-dimethyl-4H-benzo[1,4]oxazin-3-one in this step was carried out using the procedure of step 4 of Example 1 as described above to yield 4-Benzyl-2,2-dimethyl-8-piperazin-1-yl-4H-benzo[1,4]oxazin-3-one, hydrochloride salt.

Using the procedure of Example 3 using the appropriate substituted benzyl bromides, the following compounds were also prepared:

4-(4-Fluoro-benzyl)-2,2-dimethyl-8-piperazin-1-yl-4H-benzo[1,4]oxazin-3-one, hydrochloride salt. MS: (M+H) 370.

4-(3-Fluoro-benzyl)-2,2-dimethyl-8-piperazin-1-yl-4H-benzo[1,4]oxazin-3-on, hydrochloride salt. MS: (M+H) 370.

4-(3-Chloro-benzyl)-2,2-dimethyl-8-piperazin-1-yl-4H-benzo[1,4]oxazin-3-one, hydrochloride salt. MS: (M+H) 386:

4-(4-Chloro-benzyl)-2,2-dimethyl-8-piperazin-1-yl-4H-benzo[1,4]oxazin-3-one, hydrochloride salt. MS: (M+H) 386.

4-Benzyl-6-fluoro-2,2-dimethyl-8-piperazin-1-yl-4H-benzo[1,4]oxazin-3-one, hydrochloride salt. MS: (M+H) 370.

4-(4-Chloro-benzyl)-6-fluoro-2,2-dimethyl-8-piperazin-1-yl-4H-benzo[1,4]oxazin-3-one, hydrochloride salt. MS: (M+H) 405.

6-Fluoro-4-(3-fluoro-benzyl)-2,2-dimethyl-8-piperazin-1-yl-4H-benzo[1,4]oxazin-3-one, hydrochloride salt. MS: (M+H) 389.

6-Fluoro-4-(2-fluoro-benzyl)-2,2-dimethyl-8-piperazin-1-yl-4H-benzo[1,4]oxazin-3-one, hydrochloride salt. MS: (M+H) 389.

6-Fluoro-4-(4-fluoro-benzyl)-2,2-dimethyl-8-piperazin-1-yl-4H-benzo[1,4]oxazin-3-one, hydrochloride salt. MS: (M+H) 389.

4-(3-Chloro-benzyl)-6-fluoro-2,2-dimethyl-8-piperazin-1-yl-4H-benzo[1,4]oxazin-3-one, hydrochloride salt. MS: (M+H) 405.

Using the above procedure, but replacing 2-bromo-2-methyl-propionylbromide in step 1 with (R)- and (S)-2-bromo-propionylbromide, yielded the following compounds:

(R)-4-Benzyl-2-methyl-8-piperazin-1-yl-4H-benzo[1,4]oxazin-3-one, hydrochloride salt. MS: (M+H) 338: and (S)-4-Benzyl-2-methyl-8-piperazin-1-yl-4H-benzo[1,4]oxazin-3-one, hydrochloride salt. MS: (M+H) 338.

Similarly, but replacing 2-bromo-2-methyl-propionylbromide in step 1 with (1-bromo-cyclobutyl)-acetyl bromide, 4-Benzyl-2,2-spiro-cyclobutan-8-piperazin-1-yl-4H-benzo[1,4]oxazin-3-one, hydrochloride salt was prepared. MS: (M+H) 363.

Example 4

1-Benzyl-5-piperazin-1-yl-1H-benzo[1,3,4]oxathiazine 2,2-dioxide

The synthetic procedures described in this Example were carried out according to the process shown in Scheme D.

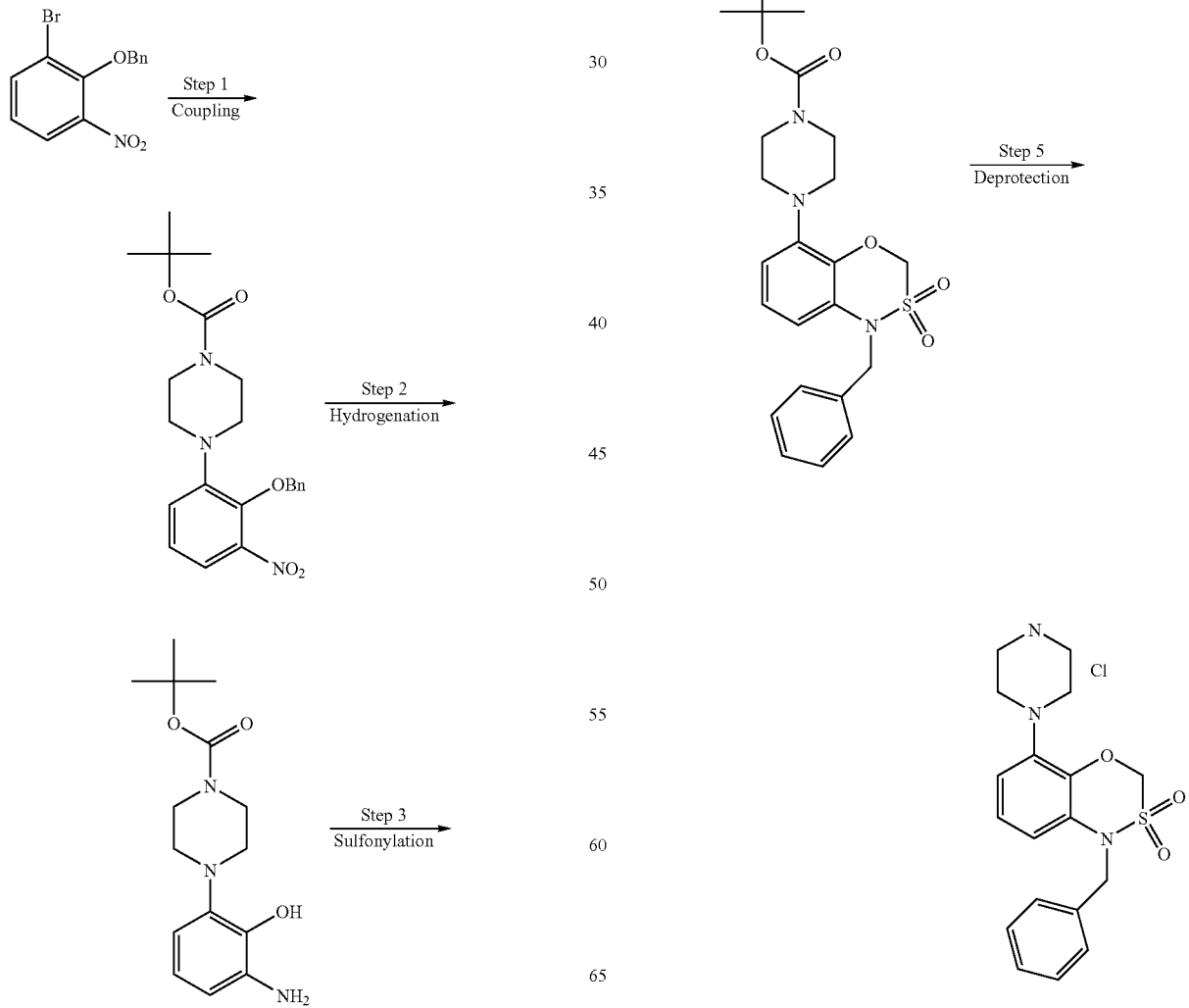

Step 1

4-(2-benzyloxy-3-nitro-phenyl)-piperazine-1-carboxylic acid tert-butyl ester

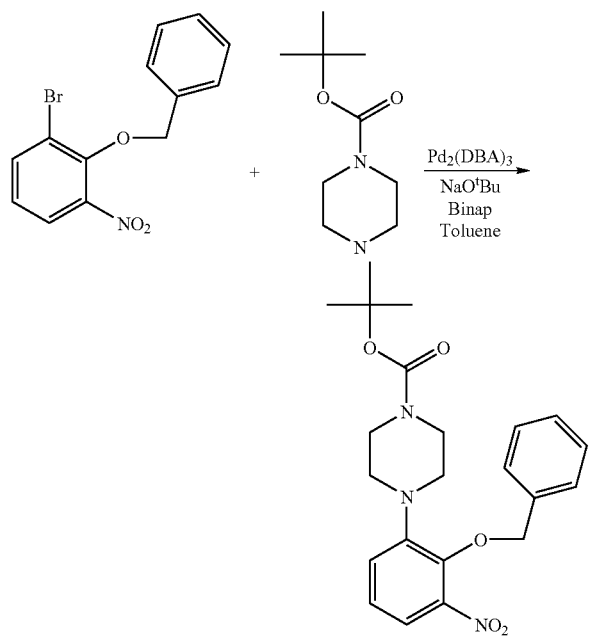

To a dry roundbottom flask was added 2-benzyloxy-1-bromo-3-nitro-benzene (9.24 g., 30 mmol), piperazine-1-carboxylic acid tert-butyl ester (6.15 g., 33 mmol), tris(dibenzylideneacetone)dipalladium(0) (1.09 g., 1.2 mmol), and rac-2,2'-bis(diphenylphosphino)-1,1'-binaphthyl (1.86 g., 3 mmol). The flask was purged with nitrogen, charged with toluene (60 mL) and warmed to 90° C. for 2.5 hours. The reaction mixture was filtered through celite, and the celite was washed with 100 mL ethyl acetate. The filtrate was concentrated in vacuo and the resulting residue was purified by flash chromatography (30% to 50% ethyl acetate in hexanes) to provide 870 mg. of 4-(2-benzyloxy-3-nitro-phenyl)-piperazine-1-carboxylic acid tert-butyl ester as a red oil (9%). $(M+H)^+=324$.

Step 2

4-(3-amino-2-hydroxy-phenyl)-piperazine-1-carboxylic acid tert-butyl ester

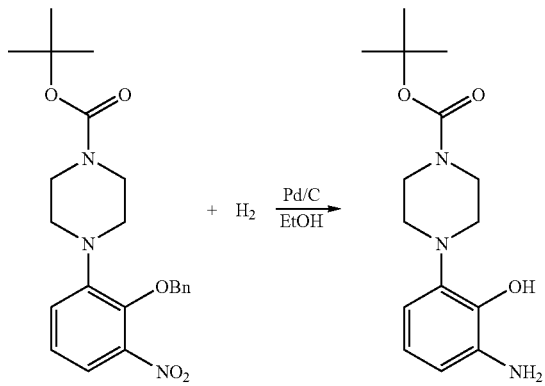

To a flask containing 10 mg. of platinum dispersed on charcoal (5%) was added 4-(2-benzyloxy-3-nitro-phenyl)-piperazine-1-carboxylic acid tert-butyl ester (680 mg., 1.65 mmol) and ethanol (5 mL). The system was purged with hydrogen by alternating application of vacuum and hydrogen gas. The resulting suspension was stirred at room temperature for 2 hours and then filtered through celite. The celite was rinsed with 45 mL ethyl acetate, and the organic solutions were combined and concentrated in vacuo to give 280 mg. of 4-(3-amino-2-hydroxy-phenyl)-piperazine-1-carboxylic acid tert-butyl ester as a brown foam (58%). $(M+H)^+=294$.

Step 3

4-(3-Chloromethanesulfonylamino-2-hydroxy-phenyl)-piperazine-1-carboxylic acid tert-butyl ester

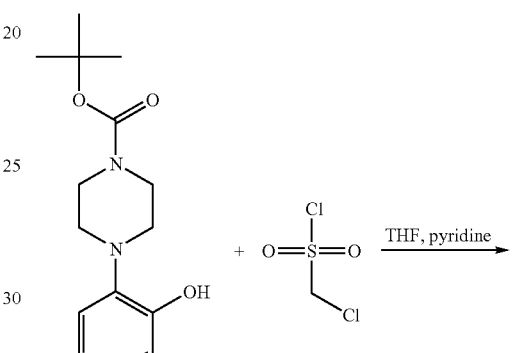

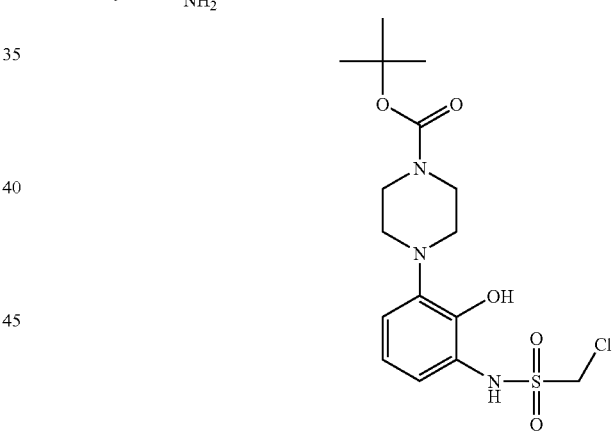

In a dry roundbottom flask, 4-(3-amino-2-hydroxy-phenyl)-piperazine-1-carboxylic acid tert-butyl ester (293 mg., 1 mmol) was dissolved in dry THF (3 mL) under nitrogen. While stirring, chloro-methanesulfonyl chloride (149 mg., 1 mmol) was added dropwise over 10 minutes and the solution was stirred 30 minutes. Pyridine (0.121 mL., 1.5 mmol) was then added dropwise over 5 minutes and the solution was stirred for 18 hours. The reaction mixture was diluted with 40 mL $Et_2O$ and washed with 40 mL of 10% aqueous HCl, 50 mL water, and 50 mL brine. The organic fraction was dried over $MgSO_4$ and concentrated in vacuo. The residue is purified by flash chromatography (20% to 40% EtOAc in hexanes) to give 190 mg of 4-(3-Chloromethanesulfonylamino-2-hydroxy-phenyl)-piperazine-1-carboxylic acid tert-butyl ester as an amber oil (45%). $(M-H)^-=404$.

Step 4

4-(1-Benzyl-2,2-dioxo-2,3-dihydro-1H-benzo[4,2,1] oxathiazin-5-yl)-piperazine-1-carboxylic acid tert-butyl ester Step 5

1-Benzyl-5-piperazin-1-yl-1H-benzo[4,2,1]oxathiazine 2,2-dioxide hydrochloride

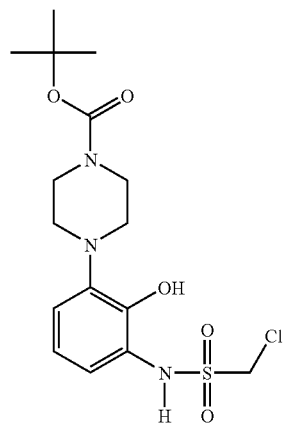

1. K$_2$CO$_3$, MeOH
2. BnBr

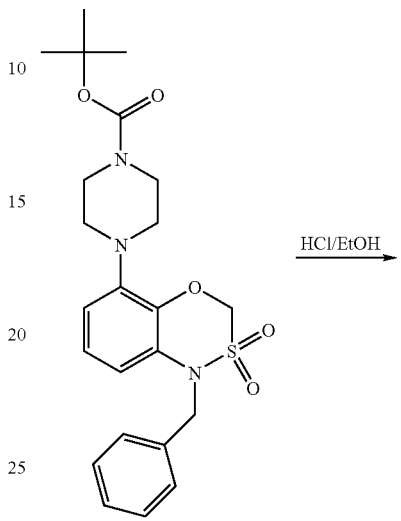

HCl/EtOH

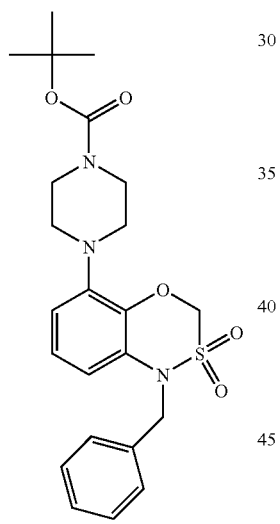

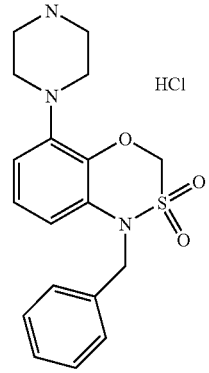

HCl

To a flask containing 7 mL methanol was added 4-(3-chloromethanesulfonylamino-2-hydroxy-phenyl)-piperazine-1-carboxylic acid tert-butyl ester (190 mg., 0.471 mmol) and potassium carbonate (195 mg, 1.4 mmol). The suspension was refluxed for two hours under nitrogen and allowed to cool to room temperature. To the reaction mixture was added benzyl bromide (0.083 mL, 0.7 mmol) and potassium carbonate (87 mg., 0.7 mmol), and the reaction was stirred at room temperature for 4 hours. The reaction mixture was concentrated in vacuo and the resulting crude solid was dissolved in ethyl acetate. The solution was washed with 50 mL water and 50 mL brine, and the ethyl acetate was removed in vacuo. The resulting residue was purified by flash chromatography to give 57 mg of 4-(1-Benzyl-2,2-dioxo-2,3-dihydro-1H-benzo[4,2,1]oxathiazin-5-yl)-piperazine-1-carboxylic acid tert-butyl ester as a light purple oil (26%). (M+H)$^+$=460

4-(1-Benzyl-2,2-dioxo-2,3-dihydro-1H-benzo[4,2,1]oxathiazin-5-yl)-piperazine-1-carboxylic acid tert-butyl ester was dissolved in 1 mL methanol and 1 mL of 2N ethanolic HCl was added. The solution is heated at 100° C. for 30 minutes, at which time was added approximately. 2 mL Et$_2$O. On cooling to room temperature, 30 mg of 1-benzyl-5-piperazin-1-yl-1H-benzo[4,2,1]oxathiazine 2,2-dioxide hydrochloride precipitated as a white solid (61%). (M+H)$^+$=360.

Example 5

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
| --- | --- |
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
| --- | --- |
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
| --- | --- |
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 6

Radioligand Binding Studies

This example illustrates in vitro radioligand binding studies of Compound of Formula I.

The binding activity of compounds of this invention in vitro was determined as follows. Duplicate determinations of ligand affinity are made by competing for binding of [$^3$H]LSD in cell membranes derived from HEK293 cells stably expressing recombinant human 5-HT6 receptor.

All determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. Assay tubes containing [$^3$H] LSD (5 nM), competing ligand, and membrane were incubated in a shaking water bath for 60 min. at 37° C., filtered onto Packard GF-B plates (presoaked with 0.3% PEI) using a Packard 96 well cell harvester and washed 3 times in ice cold 50 mM Tris-HCl. Bound [$^3$H] LSD was determined as radioactive counts per minute using Packard TopCount.

Displacement of [3H]LSD from the binding sites was quantified by fitting concentration-binding data to a 4-parameter logistic equation:

$$\text{binding} = \text{basal} + \left(\frac{Bmax - \text{basal}}{1 + 10^{-Hill(\log[\text{ligand}] - \log IC_{50})}}\right)$$

where Hill is the Hill slope, [ligand] is the concentration of competing radioligand and $IC_{50}$ is the concentration of radioligand producing half-maximal specific binding of radioligand. The specific binding window is the difference between the Bmax and the basal parameters.

Using the procedures of this Example, compounds of Formula I were tested and found to be selective 5-HT6 antagonists. Representative affinity values for the compounds of the invention are shown in Table 2.

TABLE 2

| Compound | pKi |
| --- | --- |
| 4-(2-fluoro-benzyl)-8-piperazin-1-yl-4H-benzo[1,4]oxazin-3-one | 9.04 |
| 4-(2-fluoro-benzyl)-6-fluoro-8-piperazin-1-yl-4H-benzo[1,4]oxazin-3-one | 9.17 |
| 4-Benzyl-2,2-dimethyl-8-piperazin-1-yl-4H-benzo[1,4]oxazin-3-one | 9.13 |
| (S)-4-Benzyl-2-methyl-8-piperazin-1-yl-4H-benzo[1,4]oxazin-3-one | 9.12 |
| 4-(3-Chloro-benzyl)-2,2-dimethyl-8-piperazin-1-yl-4H-benzo[1,4]oxazin-3-one | 9.12 |

Example 7

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47–59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula:

or a pharmaceutically acceptable salt or prodrug thereof, wherein:
  Y is C;
  m is 1;
  n is 1;
  p is from 0 to 3;
  q is from 1 to 3;
  Z is —$(CR^aR^b)_r$— or —$SO_2$—, where each of $R^a$ and $R^b$ is independently hydrogen or alkyl;
  r is from 0 to 2;
  X is CH or N;
  eatch $R^1$ is independently halo, alkyl, haloalkyl, heteroalkyl, alkoxy, cyano, —$S(O)_s$—$R^c$, —C(=O)—$NR^cR^d$, —$SO_2$—$NR^cR^d$, —$N(R^c)$—C(=O)—$R^d$, or —C(=O) $R^c$, where each of $R^c$ and $R^d$ is independently hydrogen or alkyl;
  s is from 0 to 2;
  $R^2$ is aryl or heteroaryl;
  each of $R^3$ and $R^4$ is independently hydrogen, alkyl, hydroxyalkyl or alkoxyalkyl, or $R^3$ and $R^4$ together with their shared carbon may form a carbocyclic ring of 3 to 6 members; and
  each of $R^5$, $R^6$, $R^7$, $R^8$ and $R^9$ is independently hydrogen or alkyl, or one of $R^5$ and $R^6$ together with one of $R^7$, $R^8$ and $R^9$ and the atoms therebetween may form a ring of 5 to 7 members.

2. The compound of claim 1, wherein Z is —$(CR^aR^b)_r$—.

3. The compound of claim 2, wherein X is N and q is 2.

4. The compound of claim 3, wherein r is 1.

5. The compound of claim 4, wherein $R^a$ and $R^b$ are hydrogen.

6. The compound of claim 5, wherein $R^2$ is optionally substituted phenyl or optionally substituted naphthyl.

7. The compound of claim 6, wherein $R^2$ is 2-halophenyl, 3-halophenyl, 4-halophenyl, naphthylen-2-yl, 3-cyanophenyl, 4-cyanophenyl, 3-nitrophenyl, 3-aminophenyl, 3-methoxyphenyl, 3-ureaphenyl, or 3-methylsulfonylamino-phenyl.

8. The compound of claim 6, wherein p is 1 and $R^1$ is halo, methyl or methoxy.

9. The compound of claim 6, wherein $R^3$ and $R^4$ are hydrogen.

10. The compound of claim 6, wherein $R^3$ and $R^4$ are methyl.

11. The compound of claim 6, wherein one of $R^3$ and $R^4$ is hydrogen and the other is methyl.

12. The compound of claim 6, wherein $R^3$ and $R^4$ together with the carbon atom therebetween form a cyclobutyl.

13. The compound of claim 7, wherein said compound is selected from:
- 4-benzyl-6-methyl-8-piperazin-1-yl-H-benzo[1,4]oxazin-3-one;
- 4-benzyl-6-methoxy-8-piperazin-1-yl-H-benzo[1,4]oxazin-3-one;
- 4-(2-fluoro-benzyl)-6-methoxy-8-piperazin-1-yl-4H-benzo[1,4]oxazin-3-one;
- 4-(2-chloro-benzyl)-6-methoxy-8-piperazin-1-yl-4H-benzo[1,4]oxazin-3-one;
- 4-(3-chloro-benzyl)-6-methoxy-8-piperazin-1-yl-4H-benzo[1,4]oxazin-3-one;
- 4-benzyl-8-piperazin-1-yl-4H-benzol[1,4]oxazin-3-one;
- 4-benzyl-6-fluoro-8-piperazin-1-yl-4H-benzo[1,4]oxazin-3-one;
- 4-(2-fluoro-benzyl)-8-piperazin-1-yl-4H-benzo[1,4]oxazin-3-one;
- 4-(4-fluoro-benzyl)-8-piperazin-1-yl-4H-benzo[1,4]oxazin-3-one;
- 4-(4-chloro-benzyl)-8-piperazin-1-yl-4H-benzo[1,4]oxazin-3-one;
- 4-(4-fluoro-benzyl)-6-fluoro-8-piperazin-1-yl-4H-benzo[1,4]oxazin-3-one;
- 4-(2-fluoro-benzyl)-6-fluoro-8-piperazin-1-yl-4H-benzo[1,4]oxazin-3-one;
- 4-(2-chloro-benzyl)-6-fluoro-8-piperazin-1-yl-4H-benzo[1,4]oxazin-3-one;
- 4-(4-chloro-benzyl)-6-fluoro-8-piperazin-1-yl-4H-benzo[1,4]oxazin-3-one;
- 6-fluoro-4-naphthalen-2-ylmethyl-8-piperazin-1-yl-4H-benzo[1,4]oxazin-3-one;
- 4-(3-chloro-benzyl)-6-fluoro-8-piperazin-1-yl-4H-benzo[1,4]oxazin-3-one;
- 3-(3-oxo-8-piperazin-1-yl-2,3-dihydro-benzo[1,4]oxazin-4-ylmethyl)-benzonitrile;
- 4-(3-fluoro-benzyl)-8-piperazin-1-yl-4H-benzo[1,4]oxazin-3-one;
- 4-benzyl-2,2-dimethyl-8-piperazin-1-yl-4H-benzo[1,4]oxazin-3-one;
- (R)-4-benzyl-2-methyl-8-piperazin-1-yl-4H-benzo[1,4]oxazin-3-one;
- 4-benzyl-6-piperazin-1-yl-4H-benzo[1,4]oxazin-3-one;
- 4-(4-Fluoro-benzyl)-6-piperazin-1-yl-4H-benzo[1,4]oxazin-3-one;
- (S)-4-Benzyl-2-methyl-8-piperazin-1-yl-4H-benzo[1,4]oxazin-3-one;
- 8-Piperazin-1-yl-4-pyridin-4-ylmethyl-4H-benzo[1,4]oxazin-3-one;
- 4-Benzyl-6-methyl-8-(4-methyl-piperazin-1-yl)-4H-benzo[1,4]oxazin-3-one;
- 4-Benzyl-8-(4-methyl-piperazin-1-yl)-4H-benzo[1,4]oxazin-3-one;
- 4-(1-Phenyl-ethyl)-8-piperazin-1-yl-4H-benzo[1,4]oxazin-3-one;
- 4-(3-Methoxy-benzyl)-8-piperazin-1-yl-4H-benzo[1,4]oxazin-3-one;
- 4-(3-Nitro-benzyl)-8-piperazin-1-yl-4H-benzo[1,4]oxazin-3-one;
- 4-(3-Amino-benzyl)-8-piperazin-1-yl-4H-benzo[1,4]oxazin-3-one;
- 3-(3-Oxo-8-piperazin-1-yl-2,3-dihydro-benzo[1,4]oxazin-4-ylmethyl)-benzonitrile;
- N-[3-(3-Oxo-8-piperazin-1-yl-2,3-dihydro-benzo[1,4]oxazin-4-ylmethyl)-phenyl]-methanesulfonamide;
- 4-(4-Fluoro-benzyl)-2,2-dimethyl-8-piperazin-1-yl-4H-benzo[1,4]oxazin-3-one;
- 4-(3-Fluoro-benzyl)-2,2-dimethyl-8-piperazin-1-yl-4H-benzo[1,4]oxazin-3-one;
- [3-(3-Oxo-8-piperazin-1-yl-2,3-dihydro-benzo[1,4]oxazin-4-ylmethyl)-phenyl]-urea;
- 4-(3-Chloro-benzyl)-2,2-dimethyl-8-piperazin-1-yl-4H-benzo[1,4]oxazin-3-one;
- 4-Benzyl-8-(3,5-dimethyl-piperazin-1-yl)-4H-benzo[1,4]oxazin-3-one;
- 4-(4-Chloro-benzyl)-2,2-dimethyl-8-piperazin-1-yl-4H-benzo[1,4]oxazin-3-one;
- 4-Benzyl-6-fluoro-2,2-dimethyl-8-piperazin-1-yl-4H-benzo[1,4]oxazin-3-one;
- 4-(4-Chloro-benzyl)-6-fluoro-2,2-dimethyl-8-piperazin-1-yl-4H-benzo[1,4]oxazin-3-one;
- 6-Fluoro-4-(3-fluoro-benzyl)-2,2-dimethyl-8-piperazin-1-yl-4H-benzo[1,4]oxazin-3-one;
- 6-Fluoro-4-(2-fluoro-benzyl)-2,2-dimethyl-8-piperazin-1-yl-4H-benzo[1,4]oxazin-3-one;
- 6-Fluoro-4-(4-fluoro-benzyl)-2,2-dimethyl-8-piperazin-1-yl-4H-benzo[1,4]oxazin-3-one;
- 4-(3-Chloro-benzyl)-6-fluoro-2,2-dimethyl-8-piperazin-1-yl-4H-benzo[1,4]oxazin-3-one;
- 4-Benzyl-8-(3,3-dimethyl-piperazin-1-yl)-4H-benzo[1,4]oxazin-3-one;
- 4-Benzyl-2,2-spiro-cyclobutan-8-piperazin-1-yl-4H-benzo[1,4]oxazin-3-one.

14. The compound of claim 5, wherein $R^2$ is heteroaryl.

15. The compound of claim 14, wherein $R^2$ is pyridine-4-yl.

16. The compound of claim 1, wherein said compound is of the formula:

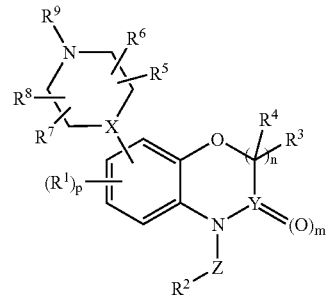

or a pharmaceutically acceptable salt or prodrug thereof, wherein X, Y, Z, $R^1$, $R^2$, $R^3$, $R^4$, $R^5$, $R^6$, $R^7$, $R^8$, $R^9$, m, n, and p are as defined in claim 1.

17. The compound of claim 1, wherein said compound is of the formula:

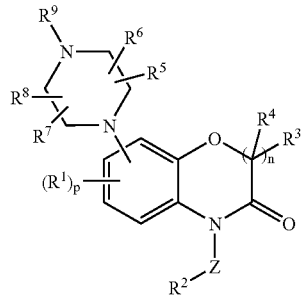

or a pharmaceutically acceptable salt or prodrug thereof, wherein Z, $R^1$, $R^2$, $R^3$, $R^4$, $R^5$, $R^6$, $R^7$, $R^8$, $R^9$, n, and p are as defined in claim 1.

18. The compound of claim 1, wherein said compound is of the formula:

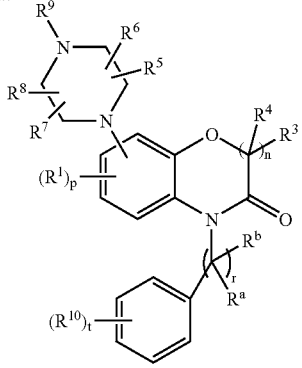

or a pharmaceutically acceptable salt or prodrug thereof, wherein $R^1$, $R^3$, $R^4$, $R^5$, $R^6$, $R^7$, $R^8$, $R^9$, $R^a$, $R^b$, n, p and r are as defined in claim 1, and wherein:
t is from 0 to 4; and
each $R^{10}$ independently is halo, alkyl, alkoxy or cyano.

19. The compound of claim 1, wherein said compound is of the formula:

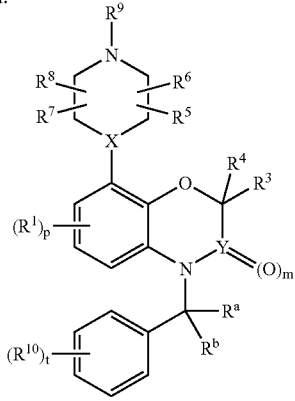

wherein X, Y, $R^1$, $R^3$, $R^4$, $R^5$, $R^6$, $R^7$, $R^8$, $R^9$, $R^a$, $R^b$, m, p and t are as recited in claim 1, and wherein:
t is from 0 to 4; and
each $R^{10}$ independently is halo, alkyl, alkoxy or cyano.

20. The compound of claim 19, wherein $R^1$ is halo, methyl or methoxy.

21. The compound of claim 19 wherein $R^3$ and $R^4$ each independently is hydrogen or methyl.

22. The compound of claim 19, wherein $R^3$ and $R^4$ together with their shared carbon form a cyclobutyl group.

23. The compound or claim 19, wherein $R^6$, $R^7$, $R^8$, $R^9$ each independently is hydrogen or methyl.

24. The compound of claim 19, wherein $R^a$ and $R^b$ each independently is hydrogen or methyl.

25. The compound of claim 19, wherein each $R^{10}$ is hydrogen, halo, nitro, cyano, amino, urea, methoxy or methanesulfonylamino.

26. A pharmaceutical composition comprising an efficacious amount of the compound of claim 1 in admixture with a pharmaceutically acceptable carrier.

27. A method for producing a substituted benzoxazinone compound, said method comprising:
(a) contacting an N-arylalkyl benzoxazinone of the formula:

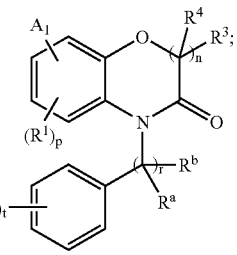

wherein:
$A_1$ is a leaving group,
n is 1;
p is from 0 to 3;
r is from 0 to 2;
t is from 0 to 4;
each of $R^a$ and $R^b$ is independently hydrogen or alkyl;
each $R^1$ is independently halo, alkyl, haloalkyl, heteroalkyl, alkoxy, cyano, —S(O)$_s$ $R^c$, —C(=O)—NR$^c$ $R^d$, —SO$_2$—NR$^c$R$^d$, —N(R$^c$)—C(=O) $R^d$, or —C(=O) R$^c$, where each of $R^c$ and $R^d$ is independently hydrogen or alkyl and s is from 0 to 2;
each of $R^3$ and $R^4$ is independently hydrogen or alkyl; and
each $R^{10}$ is independently halo, alkyl, alkoxy or cyano;
with a heterocyclic compound of the formula:

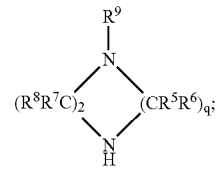

wherein:
q is from 1 to 3; and
each of $R^5$, $R^6$, $R^7$, $R^8$ and $R^9$ is independently hydrogen or alkyl, or one of $R^5$ and $R^6$ together with one of $R^7$, $R^8$ and $R^9$ may form a ring of 5 to 7 members;
in the presence of a palladium catalyst to produce the heterocyclyl-substituted N-arylalkyl benzoxaninone compound of the formula:

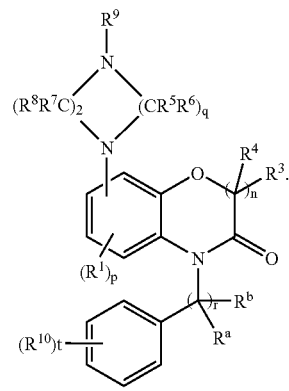

28. The method of claim 27, wherein the leaving groups $A^1$ is halo.

29. The method of claim 27, wherein the heterocyclic compound is of the formula:

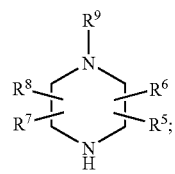

such that the heterocyclyl-substituted N-arylalkyl benzoxaninone compound is of the formula:

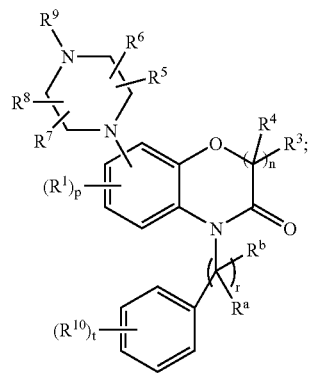

and $R^1$, $R^2$, $R^3$, $R^4$, $R^5$, $R^6$, $R^7$, $R^8$, $R^9$, $R^{10}$, n, p, r and t are as described in claim 27.

30. The method of claim 27, further comprising:
(a) contacting a benzoxazinone of the formula:

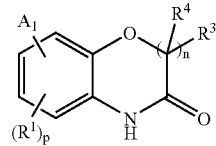

wherein n, p, $A_1$, $R^1$, $R^3$ and $R^4$ are as recited in claim 27, with an alkylating agent of the formula:

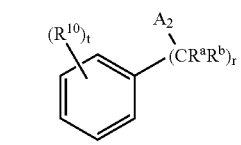

wherein:
$A_2$ is a leaving group and may the same or different from $A_1$; and
r, t, $R^a$, $R^b$ and $R^{10}$ are as recited in claim 27, to produce the N-arylalkyl benzoxazinone of the formula:

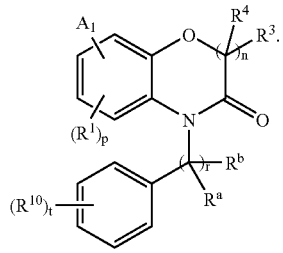

* * * * *